(12) United States Patent
Peyman

(10) Patent No.: US 10,133,056 B2
(45) Date of Patent: Nov. 20, 2018

(54) FLEXIBLE FLUIDIC MIRROR AND HYBRID SYSTEM

(71) Applicant: Gholam A. Peyman, Sun City, AZ (US)

(72) Inventor: Gholam A. Peyman, Sun City, AZ (US)

( * ) Notice: Subject to any disclaimer, the term of this patent is extended or adjusted under 35 U.S.C. 154(b) by 0 days.

(21) Appl. No.: 15/608,745

(22) Filed: May 30, 2017

(65) Prior Publication Data

US 2017/0261653 A1    Sep. 14, 2017

Related U.S. Application Data

(60) Division of application No. 14/942,256, filed on Nov. 16, 2015, now Pat. No. 9,671,607, and a
(Continued)

(51) Int. Cl.
*A61B 3/10* (2006.01)
*G02C 5/00* (2006.01)
(Continued)

(52) U.S. Cl.
CPC .......... *G02B 26/004* (2013.01); *A61B 1/0019* (2013.01); *A61B 3/12* (2013.01);
(Continued)

(58) Field of Classification Search
CPC ...... G02B 3/0056; G02B 3/14; G02B 15/173; G02B 15/14; G02B 7/08; F04B 43/046;
(Continued)

(56) References Cited

U.S. PATENT DOCUMENTS

| 4,373,218 A | 2/1983 | Schachar |
| 4,573,998 A | 3/1986 | Mazzocco |

(Continued)

OTHER PUBLICATIONS

De-Ying Zhang, Nicole Justis, Yu-Hwa Lo, "Integrated Fluidic Adaptive Zoom Lens", Optics Letters, vol. 29, Issue No. 24, pp. 2855-2857, dated Dec. 15, 2004.
(Continued)

*Primary Examiner* — Dawayne A Pinkney
(74) *Attorney, Agent, or Firm* — The Law Office of Patrick F. O'Reilly III, LLC

(57) ABSTRACT

A flexible fluidic mirror system and a hybrid fluidic optical system is disclosed herein. The flexible fluidic mirror system generally includes a flexible fluidic mirror having an outer housing and a flexible membrane supported within the outer housing, and a fluid control system operatively coupled to the flexible fluidic mirror. A portion of the flexible membrane comprises a reflective coating or film or nanoparticles disposed thereon or sprayed on. The hybrid fluidic optical system generally includes a hybrid fluidic optical device (i.e., a lens or mirror) having an outer housing and a flexible membrane supported within the outer housing, and a fluid control system operatively coupled to the hybrid fluidic optical device. The hybrid fluidic optical device further includes a magnetically actuated subsystem configured to selectively deform the flexible membrane so as to increase or decrease the convexity of the flexible membrane of the hybrid fluidic optical device.

13 Claims, 19 Drawing Sheets

Related U.S. Application Data continuation-in-part of application No. 14/461,263, filed on Aug. 15, 2014, now Pat. No. 9,191,568, which is a continuation-in-part of application No. 13/793,199, filed on Mar. 11, 2013, now Pat. No. 9,016,860, which is a continuation-in-part of application No. 13/165,231, filed on Jun. 21, 2011, now Pat. No. 8,409,278, which is a continuation-in-part of application No. 11/426,224, filed on Jun. 23, 2006, now Pat. No. 7,993,399, which is a continuation-in-part of application No. 11/259,781, filed on Oct. 27, 2005, now abandoned.

(60) Provisional application No. 62/180,668, filed on Jun. 17, 2015.

(51) Int. Cl.

| | | |
|---|---|---|
| A61B 3/14 | (2006.01) | |
| A61B 3/00 | (2006.01) | |
| G02B 1/06 | (2006.01) | |
| G02B 26/00 | (2006.01) | |
| G02B 3/14 | (2006.01) | |
| A61B 1/00 | (2006.01) | |
| A61B 3/12 | (2006.01) | |
| A61F 2/16 | (2006.01) | |
| G02B 7/28 | (2006.01) | |
| G02B 26/08 | (2006.01) | |
| G02C 7/04 | (2006.01) | |
| G02C 7/08 | (2006.01) | |
| G03B 13/32 | (2006.01) | |
| H04N 5/232 | (2006.01) | |

(52) U.S. Cl.
CPC .......... *A61B 3/1225* (2013.01); *A61F 2/1635* (2013.01); *A61F 2/1648* (2013.01); *A61F 2/1651* (2015.04); *G02B 3/14* (2013.01); *G02B 7/28* (2013.01); *G02B 26/0825* (2013.01); *G02C 7/04* (2013.01); *G02C 7/085* (2013.01); *G03B 13/32* (2013.01); *H04N 5/23212* (2013.01)

(58) Field of Classification Search
CPC ..... H01L 41/22; H01L 41/042; H01L 41/044; A45B 25/02; G11B 5/5552
USPC ....... 351/200, 205–206, 210, 219, 222, 246, 351/41, 159, 160 R, 161, 176; 359/619, 359/665–666, 676, 677, 683, 824; 417/413.2; 29/25, 35; 310/311, 317, 310/318; 360/294.4
See application file for complete search history.

(56) References Cited

U.S. PATENT DOCUMENTS

| | | |
|---|---|---|
| 4,685,921 A | 8/1987 | Peyman |
| 4,731,078 A | 3/1988 | Stoy et al. |
| 4,816,031 A | 3/1989 | Pfoff |
| 5,182,585 A | 1/1993 | Stoner |
| 6,142,630 A | 11/2000 | Koester |
| 6,186,628 B1 | 2/2001 | Van de Velde |
| 6,595,642 B2 | 7/2003 | Wirth |
| 6,673,067 B1 | 1/2004 | Peyman |
| 6,806,988 B2 | 10/2004 | Onuki et al. |
| 6,947,782 B2 | 9/2005 | Schulman et al. |
| 7,182,780 B2 | 2/2007 | Terwee et al. |
| 7,413,306 B2 | 8/2008 | Campbell |
| 8,409,278 B2 | 4/2013 | Peyman et al. |
| 9,016,860 B2 | 4/2015 | Peyman |
| 9,191,568 B2 | 11/2015 | Peyman |
| 9,671,607 B2 | 6/2017 | Peyman |
| 2002/0016629 A1 | 2/2002 | Sandstedt et al. |
| 2002/0118464 A1 | 8/2002 | Nishioka et al. |
| 2002/0149864 A1* | 10/2002 | Kaneko .............. G02B 26/0825 359/846 |
| 2003/0117719 A1* | 6/2003 | Wakai ................ G02B 13/0045 359/726 |
| 2003/0147046 A1 | 8/2003 | Shadduck |
| 2005/0140922 A1 | 6/2005 | Bekerman et al. |
| 2006/0106426 A1 | 5/2006 | Campbell |
| 2007/0046948 A1 | 3/2007 | Podoleanu et al. |
| 2007/0139751 A1* | 6/2007 | Kuiper ................ G02B 26/005 359/846 |
| 2007/0156021 A1 | 7/2007 | Morse et al. |
| 2007/0188882 A1 | 8/2007 | Cernasov |
| 2007/0211207 A1 | 9/2007 | Lo et al. |
| 2008/0030682 A1 | 2/2008 | Teige et al. |
| 2008/0158508 A1 | 7/2008 | Kawashima et al. |
| 2010/0118414 A1 | 5/2010 | Bolis |
| 2010/0157438 A1 | 6/2010 | Griffith et al. |

OTHER PUBLICATIONS

First office action on the merits (Non-Final Rejection) in U.S. Appl. No. 13/793,199, dated Jan. 9, 2014.
Second office action on the merits (Final Rejection) in U.S. Appl. No. 13/793,199, dated Mar. 6, 2014.
Third office action on the merits (Non-Final Rejection) in U.S. Appl. No. 13/793,199, dated Jul. 18, 2014.
First office action on the merits (Non-Final Rejection) in U.S. Appl. No. 14/461,263, dated Dec. 24, 2014.
Second office action on the merits (Final Rejection) in U.S. Appl. No. 14/461,263, dated Jun. 11, 2015.
First office action on the merits (Non-Final Rejection) in U.S. Appl. No. 14/942,256, dated Apr. 19, 2016.
Second office action on the merits (Final Rejection) in U.S. Appl. No. 14/942,256, dated Oct. 3, 2016.

* cited by examiner

Section A-A

Section B-B

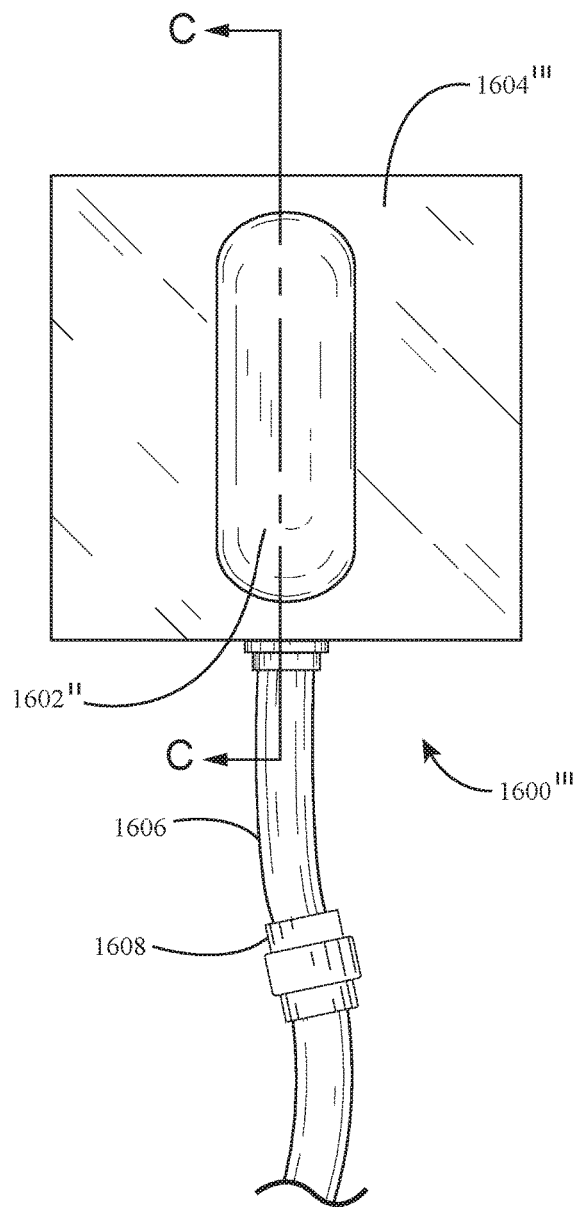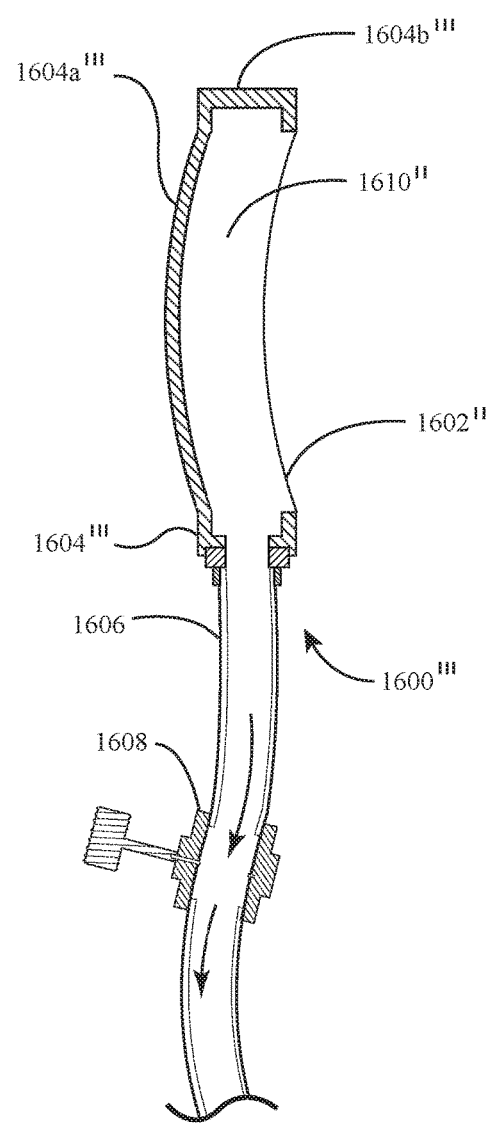
FIG. 23
Section C-C
FIG. 24

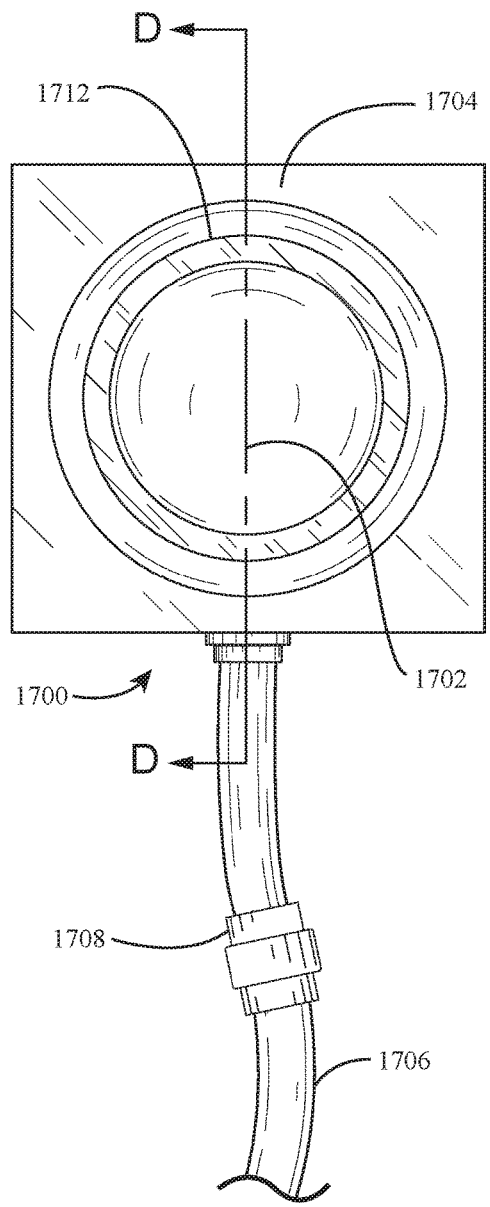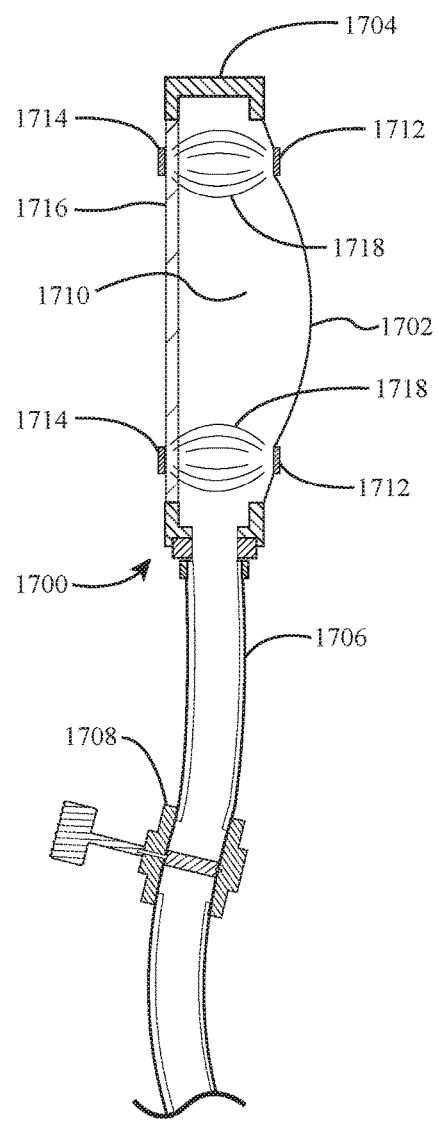
FIG. 25
Section D-D
FIG. 26

FLEXIBLE FLUIDIC MIRROR AND HYBRID SYSTEM

CROSS-REFERENCE TO RELATED APPLICATIONS

This is a divisional application of U.S. patent application Ser. No. 14/942,256, entitled "Flexible Fluidic Mirror and Hybrid System", filed on Nov. 16, 2015, which claims priority to U.S. provisional application No. 62/180,668, entitled "Flexible Fluidic Mirror and Hybrid System", filed Jun. 17, 2015, and which is a continuation-in-part of application Ser. No. 14/461,263, entitled "Automated Camera System With One Or More Fluidic Lenses", filed Aug. 15, 2014, now U.S. Pat. No. 9,191,568; which is a continuation-in-part of application Ser. No. 13/793,199 entitled "Fluidic Adaptive Optic Fundus Camera", filed Mar. 11, 2013, now U.S. Pat. No. 9,016,860; which is a continuation-in-part of application Ser. No. 13/165,231 entitled "External Lens with Flexible Membranes for Automatic Correction of the Refractive Errors of a Person", filed Jun. 21, 2011, now U.S. Pat. No. 8,409,278; which is a continuation-in-part of application Ser. No. 11/426,224 entitled "External Lens Adapted to Change Refractive Properties", filed Jun. 23, 2006, now U.S. Pat. No. 7,993,399; which is a continuation-in-part of application Ser. No. 11/259,781, entitled "Intraocular Lens Adapted for Accommodation Via Electrical Signals", filed Oct. 27, 2005, the entire contents of each of which are hereby incorporated by reference.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to a flexible fluidic mirror and a hybrid system. More particularly, the invention relates to a flexible fluidic mirror with a curvature that may be easily modified and a hybrid system with two means of adjustment.

2. Background

A normal emmetropic eye includes a cornea, lens and retina. The cornea and lens of a normal eye cooperatively focus light entering the eye from a far point, i.e., infinity, onto the retina. However, an eye can have a disorder known as ametropia, which is the inability of the lens and cornea to focus the far point correctly on the retina. Typical types of ametropia are myopia, hypermetropia or hyperopia, and astigmatism.

A myopic eye has either an axial length that is longer than that of a normal emmetropic eye, or a cornea or lens having a refractive power stronger than that of the cornea and lens of an emmetropic eye. This stronger refractive power causes the far point to be projected in front of the retina.

Conversely, a hypermetropic or hyperopic eye has an axial length shorter than that of a normal emmetropic eye, or a lens or cornea having a refractive power less than that of a lens and cornea of an emmetropic eye. This lesser refractive power causes the far point to be focused in back of the retina.

An eye suffering from astigmatism has a defect in the lens or shape of the cornea. Therefore, an astigmatic eye is incapable of sharply focusing images on the retina.

An eye can also suffer from presbyopia. Presbyopia is the inability of the eye to focus sharply on nearby objects, resulting from loss of elasticity of the crystalline lens.

Optical methods are known which involve the placement of lenses in front of the eye, for example, in the form of glasses or contact lenses, to correct vision disorders. A common method of correcting myopia is to place a "minus" or concave lens in front of the eye in order to decrease the refractive power of the cornea and lens. In a similar manner, hypermetropic or hyperopic conditions can be corrected to a certain degree by placing a "plus" or convex lens in front of the eye to increase the refractive power of the cornea and lens. Lenses having other shapes can be used to correct astigmatism. Bifocal lenses can be used to correct presbyopia. The concave, convex or other shaped lenses are typically configured in the form of glasses or contact lenses.

Also, conventional cameras are known that require the users thereof to manually adjust the focus of a lens prior to taking a photograph so that the acquired image is in-focus. The manual adjustment of the camera lens is laborious and often inaccurate. Thus, what is needed is an automated camera system that comprises means for automatically focusing the camera without the necessity for manual adjustment by the user thereof, and without the need for moving parts on the camera itself.

In addition, conventional mirrors having concave surfaces, such as those used in astronomical telescopes, are known. However, conventional concave mirrors are difficult and expensive to produce. Further, the surfaces of conventional concave, elliptical, and parabolic mirrors are not changeable because they are made of a solid material. Therefore, what is needed is a concave mirror that is relatively easy and inexpensive to produce. Moreover, concave, elliptical, and parabolic mirrors are needed that are capable of being readily adjusted when needed.

BRIEF SUMMARY OF EMBODIMENTS OF THE INVENTION

Accordingly, the present invention is directed to lens systems for the human eye, an automated camera system with one or more fluidic lenses, and a flexible fluidic mirror and hybrid system that substantially obviates one or more problems resulting from the limitations and deficiencies of the related art.

In accordance with one or more embodiments of the present invention, a lens system is provided. The lens system includes a lens adapted to be positioned along the main optical axis of the eye and a control unit. The control unit is operable with the lens to alter the focal length of the lens based at least partly upon a condition, such that the lens alters light rays and focuses the rays on the retina of the eye.

In accordance with one or more other embodiments of the present invention, a lens is provided. The lens includes a chamber adapted to house a substance. The lens is adapted to be positioned externally and relative to an eye and coupled to a control unit. The control unit is operable to control the focal length of the lens by influencing the substance, such control of the focal length altering light rays and focusing the light rays on the retina of the eye.

In accordance with yet one or more other embodiments of the present invention, a control unit is provided. The control unit includes an electronic circuit. The control unit is coupled to a lens, which includes a chamber adapted to house a substance. The lens is adapted to be positioned externally and relative to an eye. The electronic circuit is operable to control the focal length of the lens, such control of the focal length altering light rays and focusing the light rays on the retina of the eye.

In accordance with still one or more other embodiments of the present invention, an automated camera system is provided. The automated camera system includes a camera configured to capture an image of an object; at least one fluidic lens disposed between the camera and the object, the at least one fluidic lens having a chamber that receives a fluid therein; a fluid control system operatively coupled to the at least one fluidic lens, the fluid control system configured to insert an amount of the fluid into the chamber of the at least one fluidic lens, or remove an amount of the fluid from the chamber of the at least one fluidic lens, in order to change the shape of the at least one fluidic lens in accordance with the amount of fluid therein; and a Shack-Hartmann sensor assembly operatively coupled to the fluid control system, the Shack-Hartmann sensor assembly by means of the fluid control system configured to automatically control the amount of the fluid in the chamber of the at least one fluidic lens, thereby automatically focusing the camera so that the image captured of the object is in focus.

In accordance with yet one or more other embodiments of the present invention, an automated camera system is provided. The automated camera system includes a camera configured to capture an image of an object; a plurality of fluidic lenses disposed between the camera and the object, each of the plurality of fluidic lenses having a respective chamber that receives a fluid therein; a fluid control system operatively coupled to each of the plurality of fluidic lenses, the fluid control system configured to insert an amount of the fluid into the respective chamber of each of the plurality of fluidic lenses, or remove an amount of the fluid from the respective chamber of each of the plurality of fluidic lenses, in order to change the shape of each of the plurality of fluidic lenses in accordance with the amount of fluid therein; and a Shack-Hartmann sensor assembly operatively coupled to the fluid control system, the Shack-Hartmann sensor assembly by means of the fluid control system configured to automatically control the amount of the fluid in the respective chamber of each of the plurality of fluidic lenses, thereby automatically focusing the camera so that the image captured of the object is in focus.

In accordance with still one or more other embodiments of the present invention, an automated camera system is provided. The automated camera system includes a camera configured to capture an image of an object; three fluidic lenses disposed between the camera and the object, each of the three fluidic lenses having a respective chamber that receives a fluid therein; a fluid control system operatively coupled to each of the three fluidic lenses, the fluid control system configured to insert an amount of the fluid into the respective chamber of each of the three fluidic lenses, or remove an amount of the fluid from the respective chamber of each of the three fluidic lenses, in order to change the shape of each of the three fluidic lenses in accordance with the amount of fluid therein; and a Shack-Hartmann sensor assembly operatively coupled to the fluid control system, the Shack-Hartmann sensor assembly by means of the fluid control system configured to automatically control the amount of the fluid in the respective chamber of each of the three fluidic lenses, thereby automatically focusing the camera so that the image captured of the object is in focus.

In accordance with yet one or more other embodiments of the present invention, a flexible fluidic mirror system is provided. The flexible fluidic mirror system includes a flexible fluidic mirror having an outer housing and a flexible membrane supported within the outer housing, the flexible membrane at least partially defining a chamber that receives a fluid therein, a portion of the flexible membrane comprising a reflective coating or film; and a fluid control system operatively coupled to the flexible fluidic mirror, the fluid control system configured to insert an amount of the fluid into the chamber of the flexible fluidic mirror, or remove an amount of the fluid from the chamber of the flexible fluidic mirror, in order to change the shape of the flexible fluidic mirror in accordance with the amount of fluid therein.

In a further embodiment of the present invention, the reflective coating or film disposed on the flexible membrane of the flexible fluidic mirror comprises reflective nanoparticles disposed on the flexible membrane or sprayed on the flexible membrane.

In yet a further embodiment, the flexible membrane of the flexible fluidic mirror comprises a front surface that is generally circular, rectangular, or elliptical in shape, and wherein a front surface of the outer housing of the flexible fluidic mirror includes a corresponding circular, rectangular, or elliptical restrictive aperture formed therein so as to form the generally circular, rectangular, or elliptical shape of the flexible membrane front surface.

In still a further embodiment, the fluid control system comprises a pump and one or more fluid distribution lines, at least one of the one or more fluid distribution lines fluidly coupling the pump to the flexible fluidic mirror so that the pump is capable of adjusting concavity and/or convexity of the flexible fluidic mirror.

In yet a further embodiment, the flexible membrane of the flexible fluidic mirror comprises a front membrane portion disposed within a front aperture of the outer housing and a rear membrane portion disposed within a rear aperture of the outer housing such that the flexible fluidic mirror is in the form of a biconvex fluidic mirror.

In still a further embodiment, the flexible membrane of the flexible fluidic mirror is disposed within a front aperture of the outer housing, and wherein the outer housing of the flexible fluidic mirror comprises a solid, rigid rear wall that is disposed generally opposite to the flexible membrane.

In yet a further embodiment, the solid, rigid rear wall of the outer housing of the flexible fluidic mirror has a generally flat shape.

In still a further embodiment, the solid, rigid rear wall of the outer housing of the flexible fluidic mirror has a generally convex shape in order to accommodate the flexible membrane being deformed into a concave shape.

In yet a further embodiment, the fluid disposed in the chamber of the flexible fluidic mirror is in the form of a polymerizable substance so that the substance is capable of being cured after the flexible fluidic mirror is formed into a desired concave or convex shape.

In still a further embodiment, the polymerizable substance disposed in the chamber of the flexible fluidic mirror is capable of being cured by the application of at least one of: (i) ultraviolet radiation, and (ii) microwaves.

In yet a further embodiment, the reflective coating or film disposed on the flexible membrane of the flexible fluidic mirror comprises reflective nanoparticles painted on the flexible membrane or sprayed on the flexible membrane after the polymerizable substance is cured and the desired concave or convex shape of the flexible fluidic mirror is achieved.

In still a further embodiment, the polymerizable substance disposed in the chamber of the flexible fluidic mirror comprises a liquid polymer and a chemical crosslinker initiator, and wherein the flexible fluidic mirror is affixed into the desired concave or convex shape by mixing the liquid polymer with the chemical crosslinker initiator so as to solidify the flexible membrane and achieve the desired curvature.

In yet a further embodiment, the flexible fluidic mirror system further comprises a valve for regulating a flow of the fluid into, or out of, the chamber of the flexible fluidic mirror.

In accordance with still one or more other embodiments of the present invention, a hybrid fluidic optical system is provided. The hybrid fluidic optical system includes a hybrid fluidic optical device having an outer housing and a flexible membrane supported within the outer housing, the flexible membrane at least partially defining a chamber that receives a fluid therein, the hybrid fluidic optical device further including a magnetically actuated subsystem configured to selectively deform the flexible membrane so as to increase or decrease the convexity of the flexible membrane of the hybrid fluidic optical device; and a fluid control system operatively coupled to the hybrid fluidic optical device, the fluid control system configured to insert an amount of the fluid into the chamber of the hybrid fluidic optical device, or remove an amount of the fluid from the chamber of the hybrid fluidic optical device, in order to change the shape of the hybrid fluidic optical device in accordance with the amount of fluid therein.

In a further embodiment of the present invention, the hybrid fluidic optical device comprises a hybrid fluidic lens, the flexible membrane of the hybrid fluidic lens being generally transparent to light passing therethrough.

In yet a further embodiment, the flexible membrane of the hybrid fluidic optical device is disposed within a front aperture of the outer housing, and wherein the outer housing of the hybrid fluidic optical device comprises a transparent rigid rear wall that is disposed generally opposite to the flexible membrane.

In still a further embodiment, the flexible membrane of the hybrid fluidic optical device comprises a front membrane portion disposed within a front aperture of the outer housing and a rear membrane portion disposed within a rear aperture of the outer housing.

In yet a further embodiment, the hybrid fluidic optical device comprises a hybrid fluidic mirror, at least a portion of the flexible membrane of the hybrid fluidic mirror comprising a reflective coating or film disposed thereon.

In still a further embodiment, the flexible membrane of the hybrid fluidic optical device comprises a front surface that is generally circular, rectangular, or elliptical in shape, and wherein a front surface of the outer housing of the hybrid fluidic optical device includes a corresponding circular, rectangular, or elliptical restrictive aperture formed therein so as to form the generally circular, rectangular, or elliptical shape of the flexible membrane front surface.

In yet a further embodiment, the magnetically actuated subsystem of the hybrid fluidic optical device comprises an annular or rectangular ring-shaped plate disposed on a front surface of the flexible membrane and a corresponding annular or rectangular ring-shaped electromagnet disposed on a rear surface of the outer housing or flexible membrane, the annular or rectangular ring-shaped electromagnet configured to selectively displace the annular or rectangular ring-shaped plate disposed on the front surface of the flexible membrane when an electrical current is selectively applied to the electromagnet, whereby the selective displacement of the annular or rectangular ring-shaped plate by the electromagnet increases or decreases the convexity of the flexible membrane.

Additional features and advantages are described herein, and will be apparent from, the following Detailed Description and the figures.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which:

FIG. 10 is a side view in section of another embodiment of the present invention, showing the adjustable lens positioned relative to the eye;

FIG. 11 is a side view in section of another embodiment of the present invention, showing the adjustable lens as a contact lens;

FIG. 23 is a front/top view of a flexible parabolic or elliptical fluidic mirror, according to still another embodiment of the invention;

FIG. 24 is a side sectional view of the flexible parabolic or elliptical fluidic mirror of FIG. 23, wherein the section is generally cut along the cutting-plane line C-C in FIG. 23;

FIG. 25 is a front/top view of a hybrid flexible fluidic mirror, according to yet another embodiment of the invention, wherein the mirror has a circular shape and a convex configuration;

FIG. 26 is a side sectional view of the hybrid flexible fluidic mirror of FIG. 25, wherein the section is generally cut along the cutting-plane line D-D in FIG. 25;

Throughout the figures, the same parts are always denoted using the same reference characters so that, as a general rule, they will only be described once.

DETAILED DESCRIPTION OF EMBODIMENTS OF THE INVENTION

In various embodiments, a lens capable of accommodation in response to electrical signals is provided. The lens can be placed at any suitable location along the optical path of an eye, including but not limited to within the capsular bag, in place of the capsular bag, within the posterior chamber or on, in or behind the cornea. Further, it should be noted that any suitable section of the capsular bag can be removed, including but not limited to an anterior portion or a posterior portion around the main optical axis of the eye. The lens is preferably coupled to a fluidic pumping system which is also coupled to a control system which preferably includes a power source and a signal generation unit.

Figure 1:
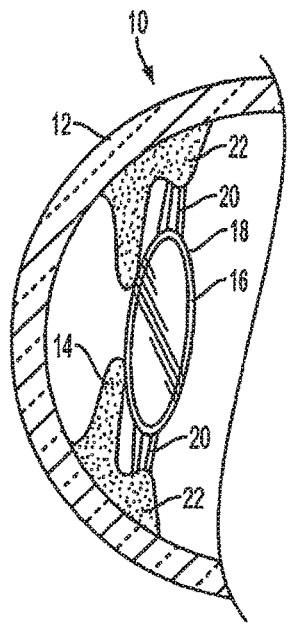
FIG. 1 is a side elevational view in section taken through the center of an eye showing the cornea, pupil, crystalline lens, and capsular bag.

Referring initially to FIG. 1, a normal eye 10 has a cornea 12, an iris 14, and a crystalline lens 16. The crystalline lens 16 is contained within a capsular bag 18 that is supported by zonules 20. The zonules 20, in turn, are connected to the ciliary muscle 22. According to Helmholz's theory of accommodation, upon contraction of the ciliary muscle 22, the tension on the zonules 20 is released. The elasticity of the lens causes the curvature of the lens 16 to increase, thereby providing increased refractive power for near vision. Conversely, during dis-accommodation, the ciliary muscle 22 is relaxed, increasing the tension on the zonules 20 and flattening the lens 16 to provide the proper refractive power for far vision.

Figure 2:
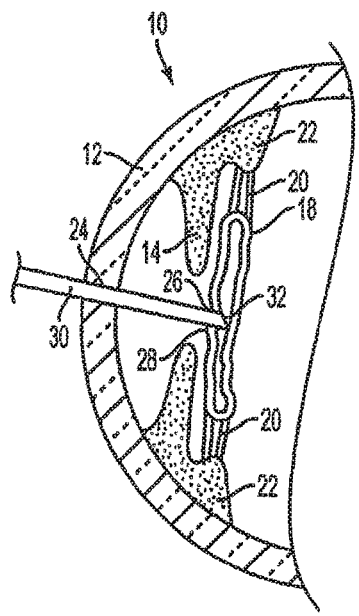
FIG. 2 is a side elevational view in section of the eye shown in FIG. 1 showing the capsular bag after removal of the crystalline lens.

If the electrically accommodating lens is to be positioned within the capsular bag and, thus, replace the crystalline lens, a suitable first step is to remove the existing lens. As illustrated in FIG. 2, the lens is preferably removed using any technique which allows removal of the lens through a relatively small incision, preferably about a 1-2 mm incision. The preferred method is to create a relatively small incision 24 in the cornea 12 and then perform a capsulorhexis to create an opening 26 into the anterior side 28 of the capsular bag 18. An ultrasonic probe 30 is inserted into the capsular bag 18 through the opening 26. The probe's vibrating tip 32 emulsifies the lens 16 into tiny fragments that are suctioned out of the capsular bag by an attachment on the probe tip (not shown). Alternatively, the lensectomy may be performed by laser phacoemulsification or irrigation and aspiration.

Once the crystalline lens 16 has been removed, the capsular bag 18 can be treated to help prevent a phenomenon known as capsular opacification. Capsular opacification is caused by the proliferated growth of the epithelial cells on the lens capsule. This growth can result in the cells covering all or a substantial portion of the front and rear surfaces of the lens capsule, which can cause the lens capsule to become cloudy and thus adversely affect the patient's vision. These cells can be removed by known techniques, such as by scraping away the epithelial cells; however, it is often difficult to remove all of the unwanted cells. Furthermore, after time, the unwanted cells typically grow back, requiring further surgery. To prevent capsular opacification, the capsular bag 18 is preferably treated to eliminate the proliferated growth of epithelial cells, as described below.

Figure 3:
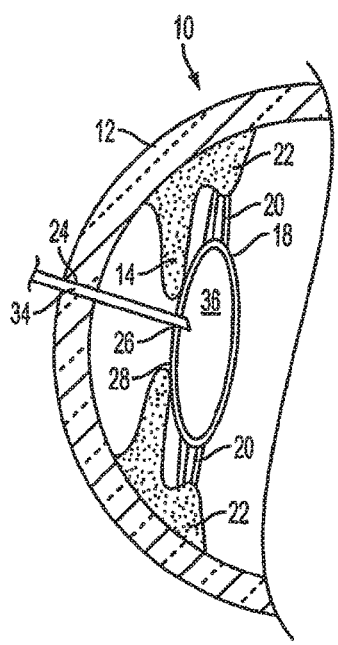
FIG. 3 is a side elevational view in section of the eye shown in FIG. 2 showing the treatment of the interior of the capsular bag with a liquid to prevent capsular opacification.

As seen in FIG. 3, one method of treating the epithelial cells to prevent capsular opacification is to use a cannula 34 to introduce a warm liquid 36 (preferably about greater 60° C.) into the capsular bag 18, filling the capsular bag 18. The liquid contains a suitable chemical that kills the remaining lens cells in the capsular bag and also cleans the interior of the capsular bag. Suitable chemicals, as well as other suitable methods of treatment that prevent capsular opacification are disclosed in U.S. Pat. No. 6,673,067 to Peyman, which is herein incorporated by reference in its entirety.

Figure 4:
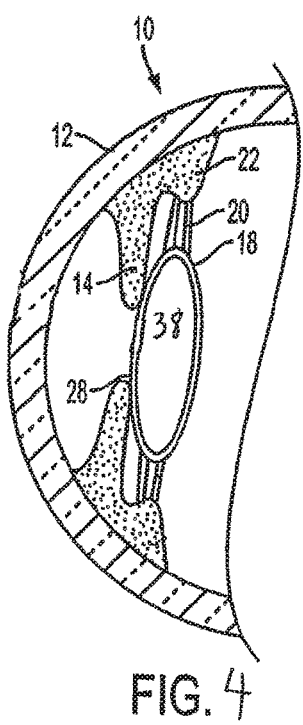
FIG. 4 is a side elevational view in section of the eye shown in FIG. 3 showing placement of a replacement lens into the capsular bag.
Figure 5:
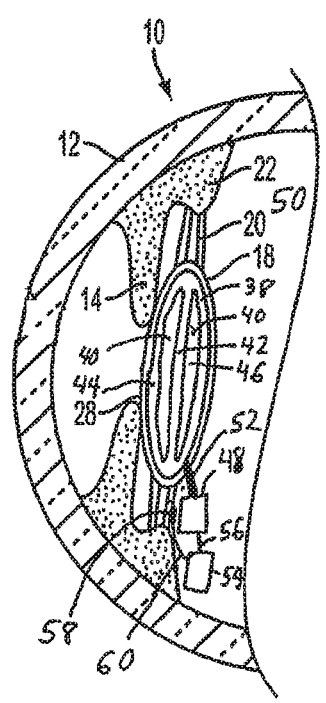
FIG. 5 is a side elevational view in section of the eye shown in FIG. 3 in which a replacement lens is positioned in the capsular bag and a fluidic system and remote power unit are positioned in the posterior chamber.

As shown in FIG. 4, a replacement lens 38 is then positioned within the capsular bag 18. Preferably, the lens 38 can be folded or rolled and inserted through the incision in the capsular bag 18; however, the lens 38 can be rigid and/or can be inserted through a larger second incision in the capsular bag 18 or the initial incision, possibly after the initial incision is widened, or in any other suitable manner. Preferably the lens 38 varies its focal length in response to changes in fluidic pressure within the lens made in accordance with electrical signals; however the lens 38 can change its index of refraction or alter its focal length in any other suitable manner. Since the capsular bag 18 is still in place, the capsular bag can still assist in accommodation;

however, it is not necessary for capsular bag 18 to assist with accommodation. The lens, as shown in FIG. 5, preferably includes two chambers 40 set on opposite sides of a substrate 42 and covered with a flexible membrane 44; however, the lens can have any or any other suitable number of chambers. Preferably, the two chambers 40 contain a fluid 46, and preferably the fluid 46 is a sodium chromate solution; however, if desired, one or more of the chambers can contain something other than a fluid or the chambers can contain different fluids or different sodium chromate solutions. The substrate 42 is preferably glass; however, the substrate 42 can be any suitable material. Preferably, the flexible membrane 44 is a biocompatible material; however, the flexible membrane can be any suitable material.

Preferably, the fluidic pressure within the chambers 40 can be altered using a fluidic system 48 which includes a miniature fluidic pressure generator (e.g., a pump or any other suitable device), a fluid flow control device (e.g., a valve or any other suitable device), a control circuit and a pressure sensor; however, the fluidic pressure can be altered in any suitable manner. Further, if desired, a fluidic system 48 does not need a pressure sensor. When subjected to an electrical signal, the electronic control circuit of the fluidic system 48 controls the valves and pumps to adjust the fluidic pressure in one or more of the chambers 40. Preferably, the fluidic pressure is adjusted by pumping fluid in or releasing a valve to allow fluid to flow out and back into the system 48; however, the fluidic pressure can be adjusted by pumping fluid out or in any other suitable manner. As a result, the shape and the focal length of the lens 38 is altered, providing accommodation. Lenses that similarly change focal length in response to fluidic pressure changes made in accordance with electrical signals are described in greater detail in "Integrated Fluidic Adaptive Zoom Lens", *Optics Letters*, Vol. 29, Issue 24, 2855-2857, December 2004, the entire contents of which is hereby incorporated by reference.

As shown in FIG. 5, fluidic system 48 is preferably positioned in the posterior chamber 50; however, the fluidic system 48 can be positioned outside the eye, within the sclera, between the sclera and the choroids or any other suitable location. Further, the fluidic system 48 is preferably positioned such that it is not in the visual pathway. A tube 52 fluidly connects the lens 38 and the fluidic system 48. Preferably, the tube 52 passes through a small incision in the capsular bag 18 near the connection of the zonules 20 and the capsular bag 18; however, the tube 52 can pass through the capsular bag in any suitable location.

Preferably, fluidic system 48 includes a power source which is preferably rechargeable through induction or other suitable means such as generating and storing electrical energy using eye and/or head movement to provide the energy to drive the generator; however, fluidic system 48 can be connected to a remote power source 54 as shown in FIG. 5 or to any other suitable power source. Preferably, the remote power source 54 is located in the posterior chamber 50; however, the remote power source 54 can be positioned outside the eye (e.g., under the scalp, within a sinus cavity, under the cheek, in the torso or in any other suitable location), within the sclera, between the sclera and the choroids or any other suitable location. Further, the remote power source 54 is preferably positioned such that it is not in the visual pathway. The remote power source 54 is preferably electrically coupled to the fluidic system 48 by electrically conductive line 56; however, the remote power source 54 can be coupled to the fluidic system 48 in any suitable manner. Further, the remote power source 54 preferably includes a signal generator which can supply control signals to the fluidic system 48 via electrically conductive line 56; however, the remote power source 54 can be without a signal generator, if desired, or can supply control signals to the fluidic system 48 in any suitable manner. Similar remote power sources are described in more detail in U.S. Pat. No. 6,947,782 to Schulman et al. which is herein incorporated by reference in its entirety.

Preferably, the remote power source 54 is coupled to a sensor 58 by electrically conductive line 60; however, the remote power source 54 can be coupled to sensor 58 in any suitable manner. The sensor 58 is preferably a tension sensor positioned on the zonules 20 so that the sensor 58 detects the amount of tension present in the zonules 20; however, the sensor 58 can be a wireless signal sensor, a neurotransmitter sensor, a chemical sensor, a pressure sensor or any other suitable sensor type and/or can be positioned in or near the ciliary muscle 22, at or near the nerve controlling the ciliary muscle 22, in the capsular bag 18 or in any other suitable location. Preferably, the sensor 58 detects the eye's attempt to cause its lens to accommodate; however, the sensor 58 can detect a manual attempt to accommodate the lens 38 (e.g., input through a wireless controller) or any other suitable input. The information detected at the sensor 58 is relayed to the remote power source 54 via line 60, and the signal generator of the remote power source 54 generates a signal in accordance with the information. The signal is sent to the fluidic system 48, which adjusts the fluidic pressure in one or more of the chambers 40 accordingly. Thus, the eye's natural attempts to focus will result in accommodation of lens 38. Response of lens 38 may vary from that of the natural lens; however, the neural systems which control the ciliary muscle 22 (and therefore the tension on the zonules 20), are provided with feedback from the optic nerve and visual neural pathways. As a result, the neural system can learn and adjust to the characteristics of the lens 38.

Figure 6:
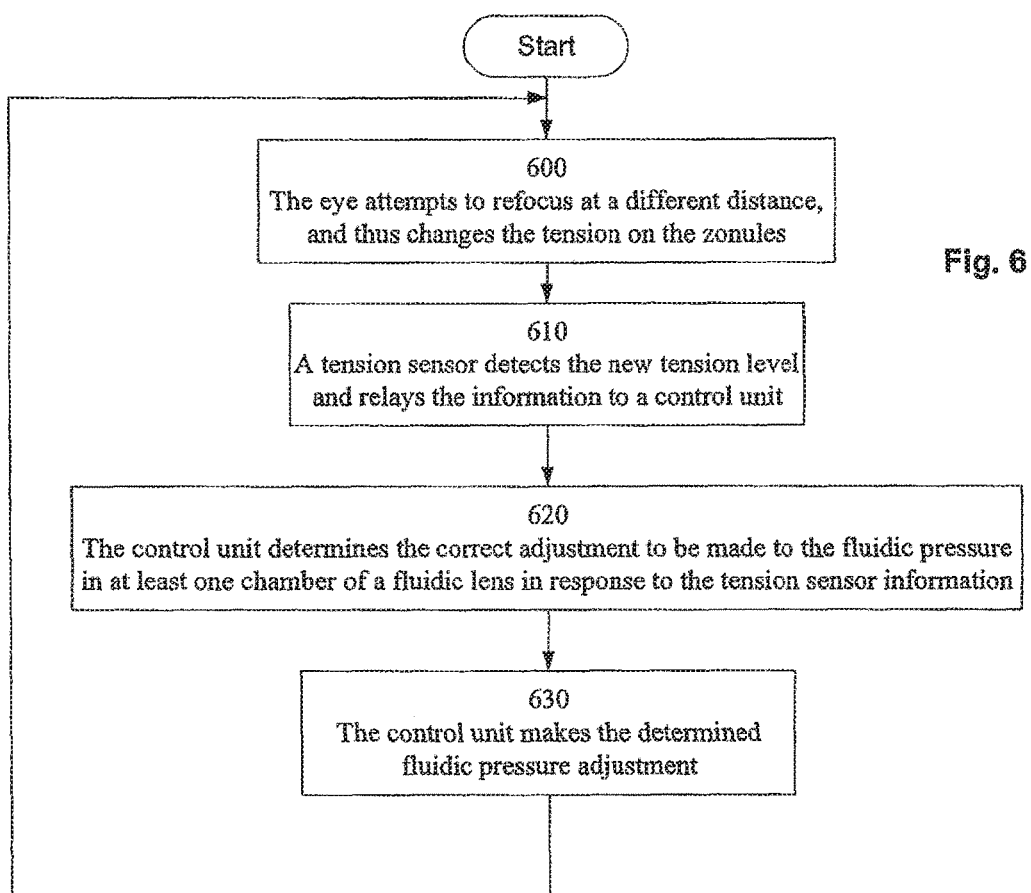
FIG. 6 is a flow chart of the process of accommodation in accordance with one embodiment of the present invention.

The process of accommodation in accordance with one embodiment is shown in FIG. 6. At step 600, the eye attempts to refocus at a different distance, and thus changes the tension on the zonules. At step 610, a tension sensor detects the new tension level and relays the information to a control unit. The control unit preferably includes a remote power source and a fluidic system; however, the control unit can include any suitable devices. At step 620, the control unit determines the correct adjustment to be made to the fluidic pressure in at least one chamber of a fluidic lens in response to the tension sensor information. At step 630, the control unit makes the determined fluidic pressure adjustment and the process repeats at step 600.

Figure 7:
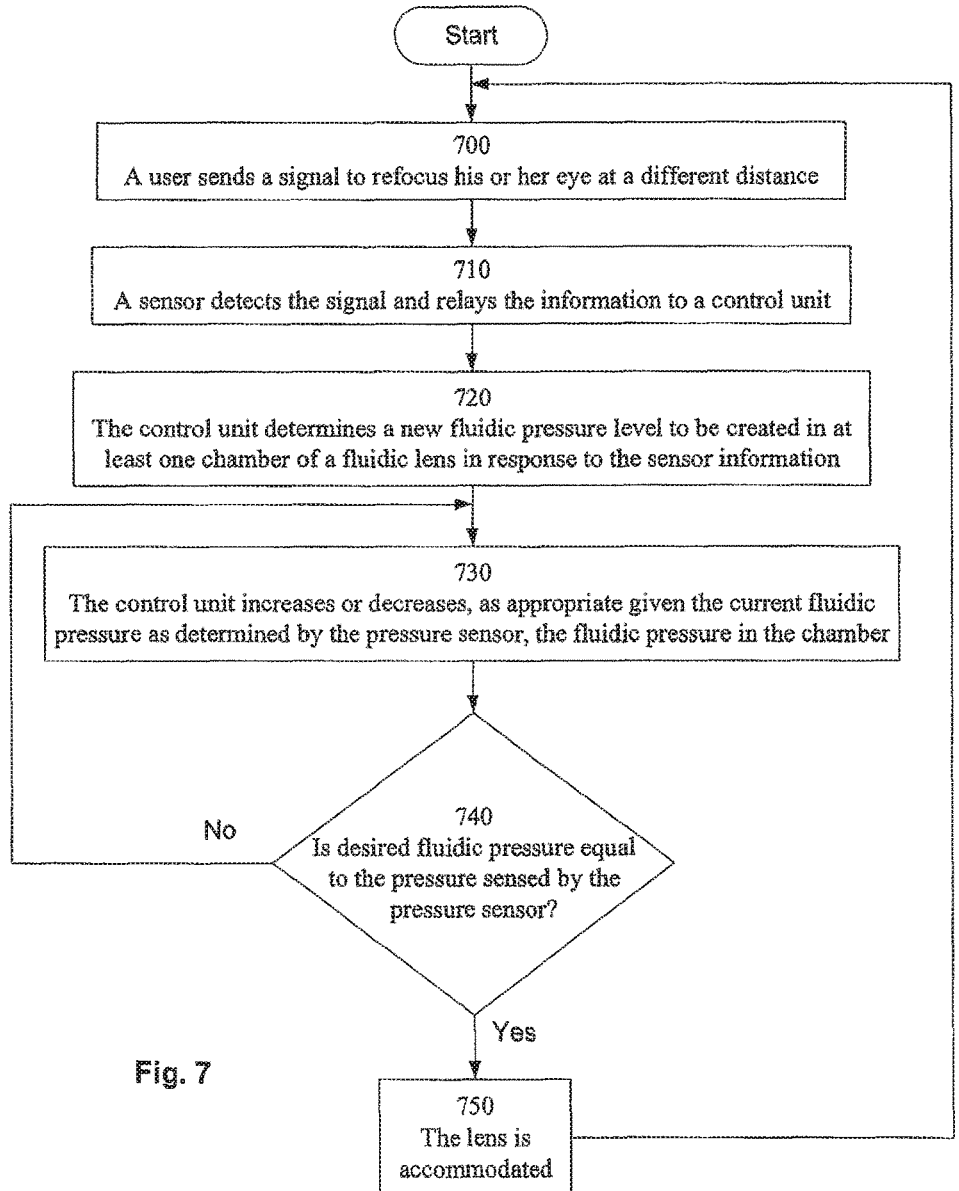
FIG. 7 is a flow chart of the process of accommodation in which the fluidic system includes a pressure sensor for sensing the pressure in at least one of the chambers in accordance with one embodiment of the present invention.

Another process of accommodation in accordance with another embodiment in which the fluidic system includes a pressure sensor for sensing the pressure in at least one of the chambers is shown in FIG. 7. At step 700, a user sends a signal to refocus his or her eye at a different distance. Preferably, the signal is sent wirelessly; however, the signal can be sent in any suitable manner. Further, the signal preferably includes information corresponding to the desired different distance; however, the signal can include information indicating only that the desired distance is closer or farther or any other suitable information. At step 710, a sensor detects the signal and relays the information to a control unit. The control unit preferably includes a remote power source and a fluidic system; however, the control unit can include any suitable devices. At step 720, the control unit determines a new fluidic pressure level to be created in at least one chamber of a fluidic lens in response to the sensor information. At step 730, the control unit increases or decreases, as appropriate given the current fluidic pressure as determined by the pressure sensor, the fluidic pressure in the chamber. At step 740, it is determined whether the desired fluidic pressure is equal to the pressure sensed by the pressure sensor. If the desired fluidic pressure is equal to the pressure sensed by the pressure sensor, at step 750, the lens is accommodated and the process repeats at step 700. If the desired fluidic pressure is not equal to the pressure sensed by the pressure sensor, the process repeats at step 730.

Figure 8:
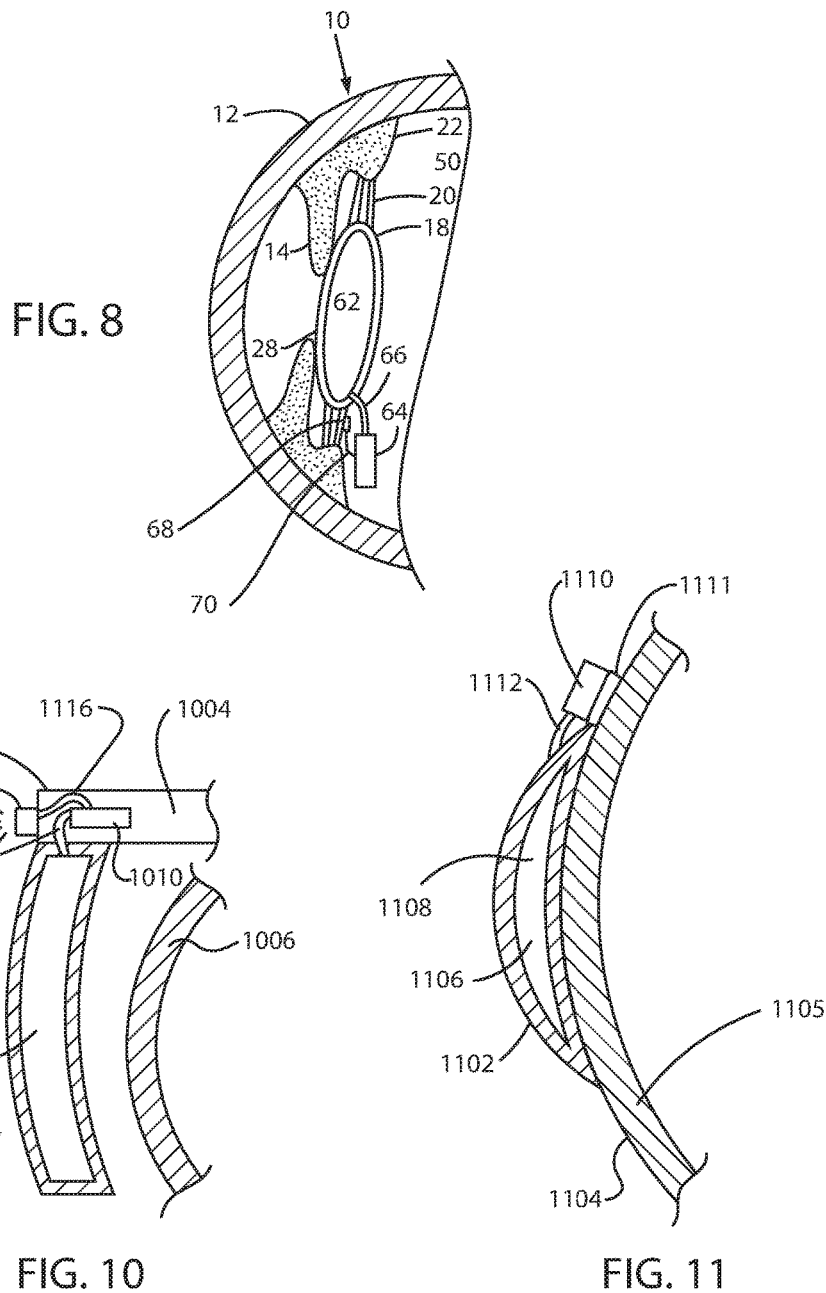
FIG. 8 is a side elevational view in section of the eye shown in FIG. 3 in which a replacement lens is positioned in the capsular bag and a power unit is positioned in the posterior chamber.

FIG. 8 illustrates an alternative accommodating lens 62. Lens 62 responds to electrical stimulation by changing its focal length. Similar to lens 38, lens 62 is preferably placed within the capsular bag 18; however, the lens 62 can be placed in the posterior chamber 50, in place of the capsular bag 18, within the cornea 12, on the surface of the eye or in any other suitable location. Further, it should be noted that any suitable section of the capsular bag can be removed, including but not limited to an anterior portion or a posterior portion around the main optical axis of the eye. If the lens 62 is placed within the capsular bag 18, the capsular bag can assist with accommodation; however, it is not necessary for the capsular bag 18 to assist with accommodation. Lens 62 may have one or more chambers that are at least partly filled with a fluid or other substance; however, lens 62 is not required to have a chamber.

Preferably, lens 62 is a fluid lens that alters its focal length by changing its shape; however lens 62 can be any suitable type of lens and can change its focal length in any suitable manner. The lens 62 preferably includes two immiscible (i.e., non-mixing) fluids of different refractive index (or other suitable optical property); however, the lens 62 is not required to include two immiscible fluids of different refractive index. Preferably, one of the immiscible fluids is an electrically conducting aqueous solution and the other an electrically non-conducting oil, contained in a short tube with transparent end caps; however, the immiscible fluids can be any suitable fluids and can be contained in any suitable container. The internal surfaces of the tube wall and one of its end caps are preferably coated with a hydrophobic coating that causes the aqueous solution to form itself into a hemispherical mass at the opposite end of the tube, where it acts as a spherically curved lens; however, the hydrophobic coating is not required and, if present, can be arranged in any suitable manner. Further, the coating can include any suitable material, including hydrophilic substances.

Preferably, the shape of the lens 62 can be adjusted by applying an electric field across the hydrophobic coating such that it becomes less hydrophobic (a process called "electrowetting" that results from an electrically induced change in surface-tension); however, the shape of the lens 62 can be adjusted by applying an electric field across any suitable portion of the lens 62. Preferably, as a result of this change in surface-tension, the aqueous solution begins to wet the sidewalls of the tube, altering the radius of curvature of the meniscus between the two fluids and hence the focal length of the lens. Increasing the applied electric field can preferably cause the surface of the initially convex lens to become less convex, substantially flat or concave; however increasing the applied electric field can cause the surface of the lens to change in any suitable manner. Preferably, decreasing the applied electric field has the opposite effect, enabling the lens 62 to transition smoothly from being convergent to divergent, or vice versa, and back again repeatably.

The lens 62 can measure 3 mm in diameter by 2.2 mm in length; however the lens 62 can have any suitable dimensions. The focal range of the lens 62 can be any suitable range and can extend to infinity. Further, switching over the full focal range can occur in less than 10 ms or any other suitable amount of time. Preferably, lens 62 is controlled by a DC voltage and presents a capacitive load; however, the lens 62 can be controlled by any suitable voltage and operate with any suitable electrical properties.

Lens 62 is electrically coupled to a power source 64 by electrically conductive line 66; however, lens 62 can be coupled to power source 64 in any suitable manner. Preferably, power source 64 is rechargeable through induction or other suitable means such as generating and storing electrical energy using eye and/or head movement to provide the energy to drive the generator; however, the power source 64 can be non-rechargeable, if desired. Similar to remote power source 54, the power source 64 is preferably located in the posterior chamber 50; however, the power source 64 can be positioned outside the eye (e.g., under the scalp, within a sinus cavity, under the cheek, in the torso or in any other suitable location), within the sclera, between the sclera and the choroids or any other suitable location. Further, the power source 64 is preferably positioned such that it is not in the visual pathway. The power source 64 preferably includes a signal generator which can supply current to the lens 62 via electrically conductive line 66; however, the power source 64 can be without a signal generator, if desired, or can supply control signals to the lens 62 in any suitable manner.

Preferably, the power source 64 is coupled to a sensor 68 by electrically conductive line 70; however, the power source 64 can be coupled to sensor 68 in any suitable manner. The sensor 68 is preferably a tension sensor positioned on the zonules 20 so that the sensor 68 detects the amount of tension present in the zonules 20; however, the sensor 68 can be a wireless signal sensor, a neurotransmitter sensor, a chemical sensor, a pressure sensor or any other suitable sensor type and/or can be positioned in or near the ciliary muscle 22, at or near the nerve controlling the ciliary muscle 22, in the capsular bag 18 or in any other suitable location. Preferably, the sensor 68 detects the eye's attempt to cause its lens to accommodate; however, the sensor 68 can detect a manual attempt to accommodate the lens 62 (e.g., input through a wireless controller) or any other suitable input. The information detected at the sensor 68 is relayed to the power source 64 via line 70, and the signal generator of the power source 64 generates a signal in accordance with the information. The signal is sent and passed through the lens 62, which preferably changes shape as a result of the electrical current flowing through it; however, the lens 62 could change its index of refraction in response to the electrical current flowing through it or change its focal length in any other suitable manner. Preferably, line 70 includes two separate electrical pathways that electrically couple to lens 62 at different, preferably substantially opposite, locations so that one of the pathways can serve as a ground wire; however, the lens 62 can be grounded in any other suitable manner to enable current supplied via line 70 to flow through the lens 62. As a result, similar to lens 38, the eye's natural attempts to focus will result in accommodation of lens 62. Response of lens 62 may vary from that of the natural lens; however, as with lens 38, the neural systems which control the ciliary muscle 22 (and therefore the tension on the zonules 20), are provided with feedback from the optic nerve and visual neural pathways. As a result, the neural system can learn and adjust to the characteristics of the lens 62.

Figure 9:
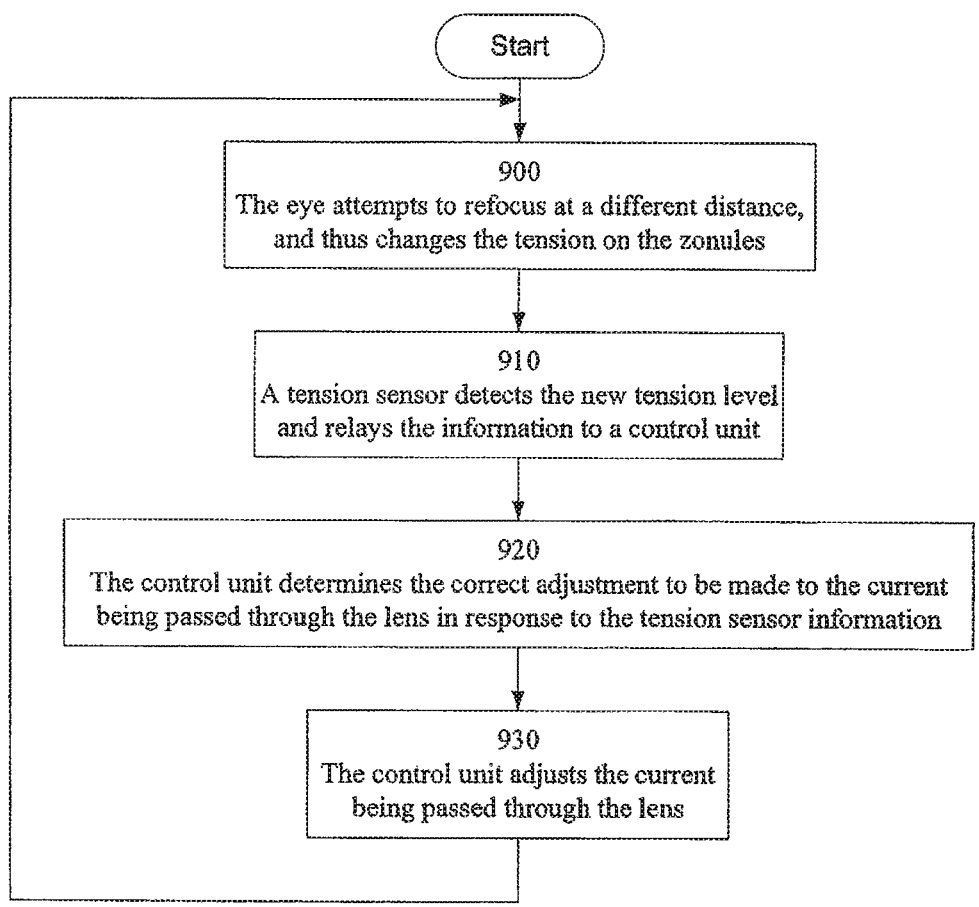
FIG. 9 is a flow chart of the process of accommodation in response to electrical signals in accordance with one embodiment of the present invention.

The process of accommodation in response to electrical signals in accordance with one embodiment is shown in FIG. 9. At step 900, the eye attempts to refocus at a different distance, and thus changes the tension on the zonules. At step 910, a tension sensor detects the new tension level and relays the information to a control unit. The control unit preferably includes a power source; however, the control unit can include any suitable devices. At step 920, the control unit determines the correct adjustment to be made to the current being passed through the lens in response to the tension sensor information. At step 930, the control unit adjusts the current being passed through the lens and the process repeats at step 900.

In another embodiment, as illustrated in FIGS. 10-11, the present invention can be used in an external lens. For example, the lens can be configured to be used with spectacles (FIG. 10) or as a contact lens (FIG. 11). The embodiments of FIG. 10-11 are configured to correct refractive errors in the eye. For example, the present embodiments can correct at least myopia, hyperopia and astigmatism. Furthermore, since these embodiments (as discussed in more detail below) can have their refractive properties altered, they are multi-focal lenses. Thus, these lenses can correct, among other disorders, presbyopia, or any combination of disorders.

When configured to be used in conjunction with spectacles 1000, lens 1002 is preferably coupled to a frame 1004 that positions the lens 1002 relative to the cornea 1006 of the eye in any suitable manner. As with previous embodiments, the lens 1002 has a chamber or area 1008 (or multiple chambers or areas, if desired) that is configured to hold a fluid or a mixture of fluids or any other suitable substance. Chamber 1008 preferably includes two immiscible (i.e., non-mixing) fluids of different refractive index (or other suitable optical property); however, the chamber 1008 is not required to include two immiscible fluids of different refractive index. Preferably, one of the immiscible fluids is an electrically conducting aqueous solution and the other an electrically non-conducting oil, contained in a short tube with transparent end caps, as described above; however, the immiscible fluids can be any suitable fluids and can be contained in any suitable container. The above description of the fluids is applicable to the present invention.

Preferably, as with the embodiments above, the shape of the lens 1002 can be adjusted by applying an electric field across the hydrophobic coating such that it becomes less hydrophobic (a process called "electrowetting" that results from an electrically induced change in surface-tension); however, the shape of the lens 1002 can be adjusted by applying an electric field across any suitable portion of the lens 1002. Preferably, as a result of this change in surface-tension, the aqueous solution begins to wet the sidewalls of the tube, altering the radius of curvature of the meniscus between the two fluids and hence the focal length of the lens. Increasing the applied electric field can preferably cause the surface of the initially convex lens to become less convex, substantially flat or concave; however increasing the applied electric field can cause the surface of the lens to change in any suitable manner. Preferably, decreasing the applied electric field has the opposite effect, enabling the lens 1002 to transition smoothly from being convergent to divergent, or vice versa, and back again repeatably. Thus, allowing the lens 1002 to repeatably focus on near and/or far objects.

The focal range of the lens 1002 can be any suitable range and can extend to infinity. Further, switching over the full focal range can occur in less than 10 ms or any other suitable amount of time. Preferably, lens 1002 is controlled by a DC voltage and presents a capacitive load; however, the lens 1002 can be controlled by any suitable voltage and operate with any suitable electrical properties.

Lens 1002 is electrically coupled to a power source 1010 by electrically conductive line 1012; however, lens 1002 can be coupled to power source 1010 in any suitable manner. Preferably, power source 1010 is rechargeable through direct electrical current, induction or other suitable means such as generating and storing electrical energy using eye and/or head movement to provide the energy to drive the generator; however, the power source 1010 can be non-rechargeable, if desired. Power source 1010 is preferably located on the frame 1004 of spectacles 1000; however, the power source 1010 can be positioned in any suitable location. The power source 1010 preferably includes a signal generator which can supply current to the lens 1002 via electrically conductive line 1012; however, the power source 1010 can be without a signal generator, if desired, or can supply control signals to the lens 1002 in any suitable manner.

Preferably, the power source 1010 is coupled to a sensor 1114 by electrically conductive line 1116; however, the power source 1010 can be coupled to sensor 1116 in any suitable manner (e.g. wirelessly). The sensor 1114 is preferably a distance sensor positioned on the front 1118 of frame 1004 so that the sensor 1114 detects the distance of an object away from the eye (such as a laser range finder); however, the sensor 1114 can be any suitable sensor type. Preferably, the sensor 1114 is positioned relative to the eye such that it detects the distance a specific object is from the eye and adjusts the lens 1002 accordingly; however, the sensor 1114 can detect a manual attempt to adjust the lens 1002 (e.g., input through a wireless controller or direct push buttons) or any other suitable input. The information detected at the sensor 1114 is relayed to the power source 1010 via line 1116, and the signal generator of the power source 1010 generates a signal in accordance with the information. The signal is sent and passed through the lens 1002, which preferably changes shape as a result of the electrical current flowing through it; however, the lens 1002 could change its index of refraction in response to the electrical current flowing through it or change its focal length in any other suitable manner. Preferably, line 1012 includes two separate electrical pathways that electrically couple to lens 1102 at different, preferably substantially opposite, locations so that one of the pathways can serve as a ground wire; however, the lens 1002 can be grounded in any other suitable manner to enable current supplied via line 1012 to flow through the lens 1002.

Additionally, the lens 1002 can be wirelessly coupled to a sensor, such as sensor 68, described above and adjust based on signals from the cilliary muscles and/or the zonules. Response of lens 1002 may vary from that of the natural lens; however, as with lenses described above, the neural systems which control the ciliary muscle 22 (and therefore the tension on the zonules 20), are provided with feedback from the optic nerve and visual neural pathways. As a result, the neural system can learn and adjust to the characteristics of the lens 1002.

FIG. 11 illustrates another embodiment of the present invention, where the lens 1102 is a contact lens that is positioned on the external surface 1104 of the cornea 1105.

As with lens 1002, lens 1102 includes a chamber or area 1106 (or multiple chambers or areas, if desired) having a fluid 1108 therein. Preferably, fluid 1108 is the same as the fluid described above for lens 1002 and operates in the substantially the same manner; however, any suitable fluid and/or substance or combination thereof can be used.

As described above, lens 1102 is coupled to a power source 1110 via an electrical wire 1112, or by any other suitable means. The power source 1110 is coupled to lens 1102 in any suitable manner (e.g., attached to a protrusion 1111). Power source 1110 and electrical wire 1112 are configured and operate in substantially the same manner as described above for lens 1002. Any description of lens 1002 and power source 1010 is applicable to lens 1102 and power source 1110.

Furthermore, lens 1102 can have a distance sensor (or any other sensor) that is located outside the eye and wirelessly coupled or directly wired to power source 1110, as described above. The sensor can be a sensor coupled to the lens 1102 (or any other suitable place on or adjacent the eye) or it can be located in the eye, and operate in substantially the same manner as sensors described above.

Additionally, both lens 1002 and 1102 can have their respective refractive properties altered in any manner described herein and are not limited the specific descriptions above. For example, lens 1102 and lens 1002 can have their respective refractive properties altered by changing the fluidic pressure as described above.

Figure 12:
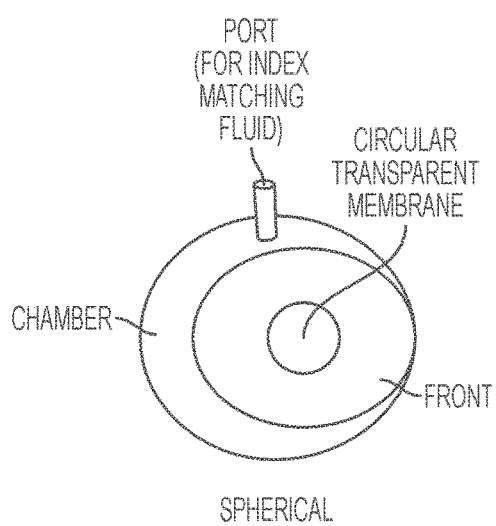
FIG. 12 illustrates a fluidic spherical lens in accordance with one embodiment of the present invention.
Figure 13:
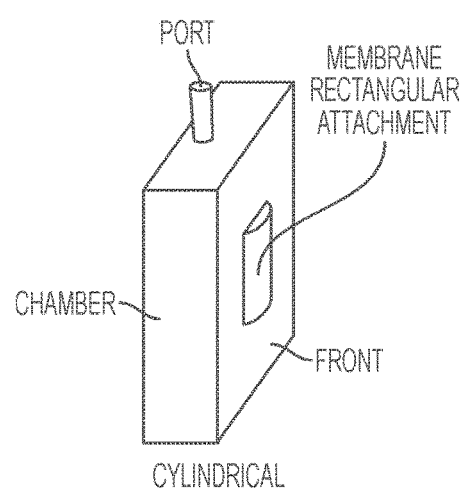
FIG. 13 illustrates a fluidic cylindrical lens in accordance with one embodiment of the present invention.
Figure 14:
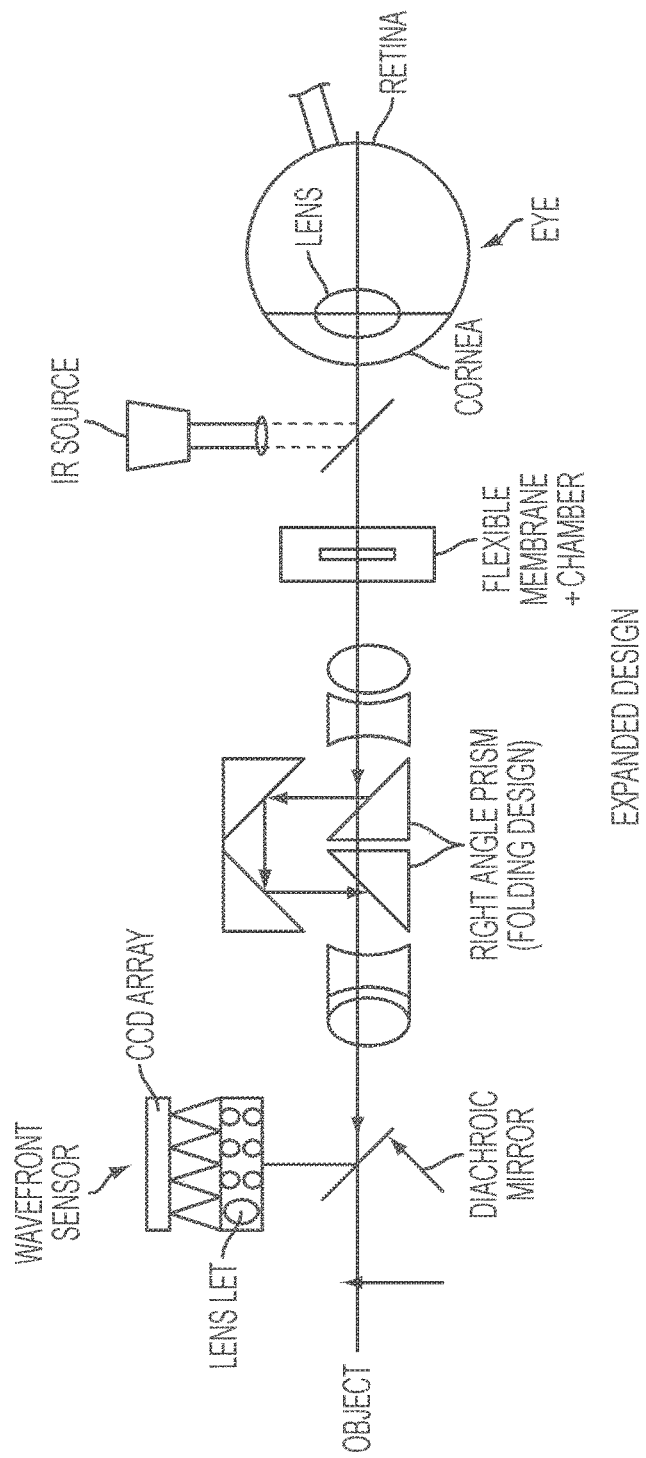
FIG. 14 illustrates another embodiment of the present invention in which a device is shown that is capable of automatically correcting all refractive errors of an eye.

As shown in FIGS. 12, 13, and 14, one embodiment of the automated system of the present invention comprises flexible membrane, similar to the embodiments described above, attached to a solid chamber where the membrane's surface can be made to act as a positive or negative surface by altering the fluid pressure inside the chamber.

The membrane can be constructed from any transparent elastomeric material. Depending on the membrane's peripheral attachment (e.g. circular) the membrane acts as a spherical (plus or minus 35.00 D) lens or (plus or minus 8.00 D) cylindrical lens when its attachment is rectangular (FIGS. 12-13).

By combining one spherical and two cylindrical lens-membranes, positioned 45 degrees to one another, one can correct all low order aberration of the refractive errors.

Using a non-uniform thickness membrane or an additional lens module one can also correct the higher order aberrations of refractive errors and creation of an achromatic lens. The flexible membrane lens is adjusted to null the wavefront error of the eye.

When this system is combined with a relay telescope, the image of the eye pupil can be projected onto a wavefront sensor via a diachroic mirror to analyze the shape of the wavefront (FIG. 14) while the person sees a near or distant object. The present system eliminates deformable mirrors and scanning parts; therefore it is a compact and stable unit.

The sensor in return corrects automatically all refractive errors of an eye by adding or subtracting fluid from the chamber holding the flexible membrane, thereby adjusting the curvature of the flexible membranes.

The final information is equal to the eye's refractive power of an eye for any given distance. Because of its simple design and light weight of the system both eyes of a person can be corrected simultaneously.

Additional application of this concept besides vision correction and photography includes microscope lenses, operating microscope, a lensometer capable of measuring accurately various focal points (power) of a multifocal lens or a multifocal diffractive lens, liquid crystal lenses etc. known in the art. A combination of the plus and minus flexible membrane lenses can also provide a lightweight telescope. Others include hybrid combination of this technology with diffractive, refractive and liquid crystal lenses.

Figure 15:
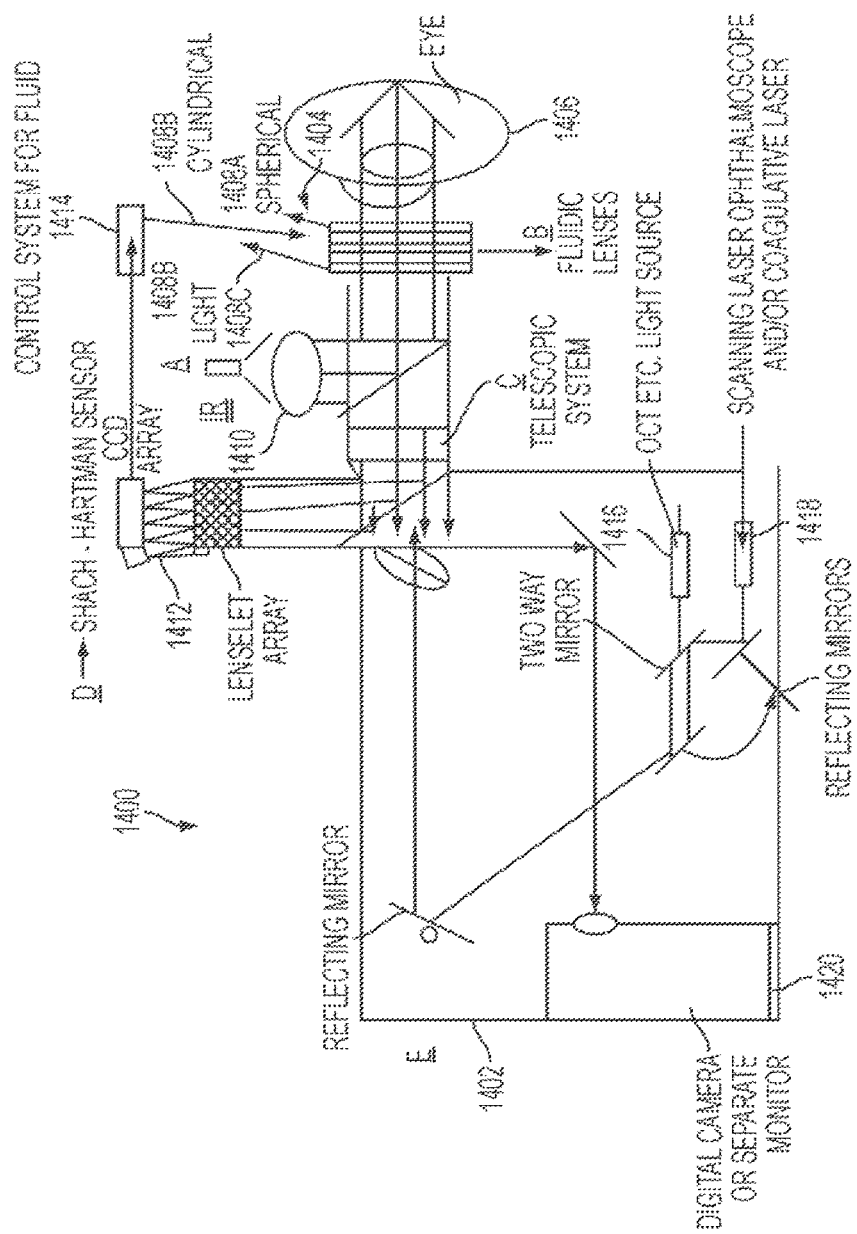
FIG. 15 illustrates another embodiment of the present invention in which a fluidic adaptive optic fundus camera is shown.

FIG. 15 illustrates another embodiment of the present invention. In particular, FIG. 15 illustrates a system 1400 in which a fundus camera 1402 uses a fluidic adaptive optic lens 1404. Adjacent the patient's eye 1406, are the three fluidic lenses 1408A-C. Preferably, one of the fluidic lenses is a spherical lens 1408A, and two of the lenses are cylindrical lenses 1408B and 1408C. However, the system can include any number of suitable lenses. In an exemplary embodiment, the spherical lens 1408A is disposed in a first plane, the first cylindrical lens 1408B is disposed in a second plane, and the second cylindrical lens 1408C is disposed in a third plane. Each of the first, second, and third planes are oriented parallel or generally parallel to one another. Also, the first cylindrical lens 1408B has a first axis and the second cylindrical lens 1408C has a second axis. The first axis of the first cylindrical lens 1408B is disposed at an angle of approximately 45 degrees relative to the second axis of the second cylindrical lens 1408C. In addition, in an exemplary embodiment, the first plane of the spherical lens 1408A is disposed closer to the eye 1406 than the second plane of the first cylindrical lens 1408B and the third plane of the second cylindrical lens 1408C. As such, in this exemplary embodiment, the cylindrical lenses 1408B, 1408C are positioned at 45 degrees or about 45 degrees relative to each other, and are disposed in front of the spherical lens 1408A (i.e., farther from the eye 1406).

The three lens system forms a telescopic system that transmits the light from IR light 1410 reflected from the eye and through the three lenses to a Shack-Hartmann sensor 1412. The Shack-Hartmann sensor is connected to control system 1414 through a charge-coupled device (CCD) array. The Shack-Hartmann sensor and the control system controls the amount of fluid injected and/or removed in the three fluidic lenses. Preferably, the control system includes (or is in communication with) a pump (not shown) which injects and withdraws fluid from a container (not shown). By injecting and withdrawing fluid from the lenses, high and low order aberrations are eliminated prior to the photography, since the fluidic lenses are capable of adjusting to the specific needs of the eye, in the same manner as described above.

Fundus camera 1402 is preferably equipped with white flush or a scanning laser ophthalmoscope or various lasers with different wavelengths from ultraviolet to infra-red wave length to obtain various visual information from the retina, choroid and optic nerve head. At low energy, the coagulative laser 1418 in FIG. 15 acts as an aiming beam, so it may be both coagulative and non-coagulative depending on its energy level. An Optical coherence tomography (OCT) 1416 or a laser can replace the scanning laser 1418 (or coagulative laser) to obtain two or three dimensional histological images from the eye structures or the laser can perform a precise coagulation of the retina along with the OCT images.

The fundus camera 1402 is also connected to a digital camera 1420 and/or a visualization monitor. Therefore, the images captured by the fundus camera can be viewed in real time or captured for viewing at a later time.

Additionally, the camera position can be moved into any desired position by a two way mirror that is positioned behind the fluidic lens.

The present system results in a compact, lightweight, precise and inexpensive advanced camera system eliminating the need for the complex prior technology which uses deformable mirrors.

Figure 16:
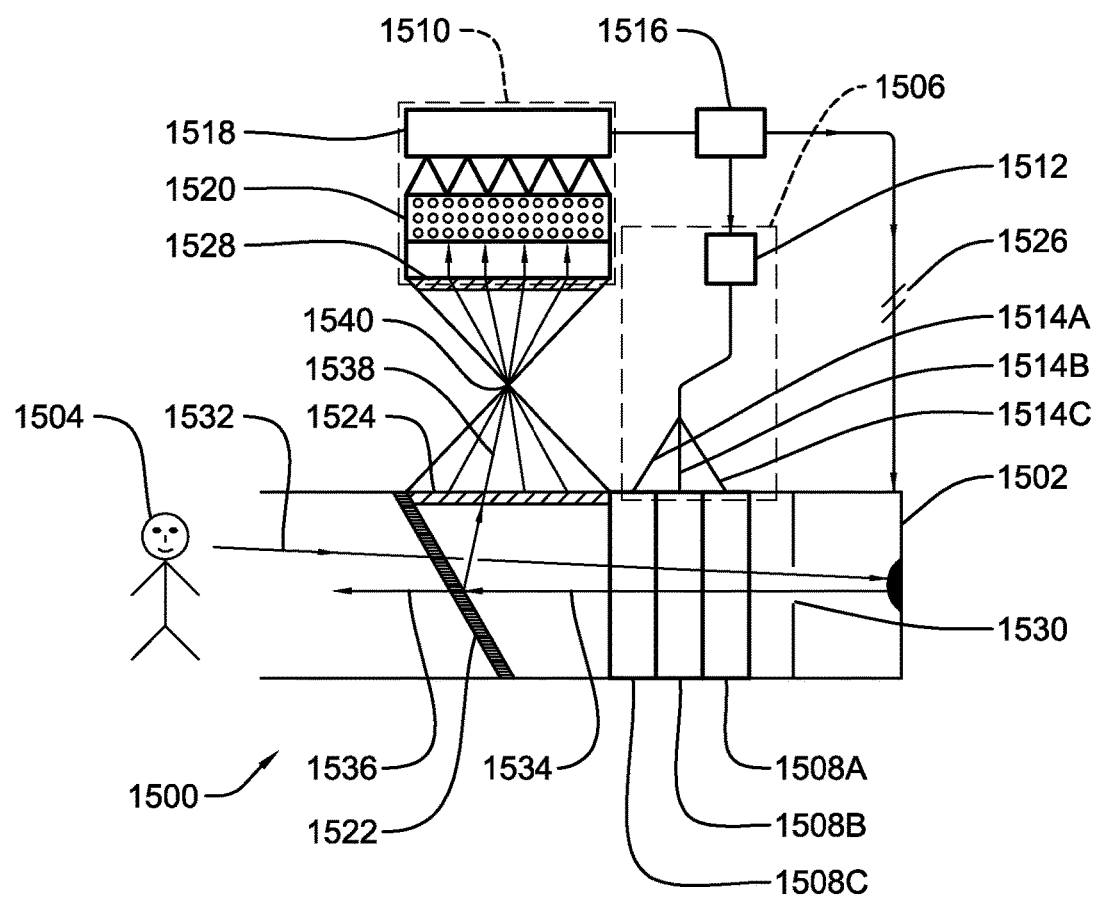
FIG. 16 illustrates yet another embodiment of the present invention in which an automated camera system is shown, wherein the automated camera system comprises a plurality of fluidic lenses.

FIG. 16 illustrates yet another embodiment of the present invention. In particular, FIG. 16 illustrates an automated camera system 1500, wherein the light waves entering a camera are corrected using a plurality of fluidic lenses 1508A, 1508B, and 1508C. As shown in FIG. 16, the automated camera system 1500 generally comprises a camera 1502 configured to capture an image of an object 1504; a plurality of fluidic lenses (e.g., three fluidic lenses 1508A, 1508B, and 1508C) disposed between the camera 1502 and the object 1504, each of the plurality of fluidic lenses 1508A, 1508B, and 1508C having a respective chamber that receives a fluid therein; a fluid control system 1506 operatively coupled to each of the plurality of fluidic lenses 1508A, 1508B, and 1508C, the fluid control system 1506 configured to insert an amount of the fluid into the respective chamber of each of the plurality of fluidic lenses 1508A, 1508B, and 1508C, or remove an amount of the fluid from the respective chamber of each of the plurality of fluidic lenses 1508A, 1508B, and 1508C, in order to change the shape of each of the plurality of fluidic lenses 1508A, 1508B, and 1508C in accordance with the amount of fluid therein; and a Shack-Hartmann sensor assembly 1510 operatively coupled to the fluid control system 1506, the Shack-Hartmann sensor assembly 1510 by means of the fluid control system 1506 configured to automatically control the amount of the fluid in the respective chamber of each of the plurality of fluidic lenses 1508A, 1508B, and 1508C, thereby automatically focusing the camera 1502 so that the image captured of the object 1504 is in focus. The camera 1502 may comprise any one of: (i) a digital camera for photography, (ii) a camera for automated microscopy, (iii) an optical coherence tomography (OCT) camera, (iv) a video surveillance camera, or (v) a camera for any other form of imaging, such as telesystem imager or a laser scanner, etc. The camera 1502 may record visible light images, infrared (IR) light images, ultraviolet (UV) light images, etc. Advantageously, the camera 1502 has no moving parts and is automatically focused by means of the plurality of fluidic lenses 1508A, 1508B, and 1508C.

As shown in FIG. 16, the camera 1502 comprises a camera aperture 1530 that allows light rays to pass therethrough. The camera 1502 may also comprise a standard lens that is disposed behind the plurality of fluidic lenses 1508A, 1508B, and 1508C.

In the automated camera system 1500 of FIG. 16, the three fluidic lenses may include a spherical lens 1508A, a first cylindrical lens 1508B, and a second cylindrical lens 1508C. In the illustrated embodiment, the spherical lens 1508A, which is closest to the camera 1502, may be a spherical lens as illustrated in FIG. 12. Similarly, in the illustrated embodiment, the first and second cylindrical lenses 1508B, 1508C, which are disposed in front of the spherical lens 1508A, may each be a cylindrical lens as illustrated in FIG. 13. In an exemplary embodiment, the spherical lens 1508A is disposed in a first plane, the first cylindrical lens 1508B is disposed in a second plane, and the second cylindrical lens 1508C is disposed in a third plane. Each of the first, second, and third planes are oriented parallel or generally parallel to one another. Also, the first cylindrical lens 1508B has a first axis and the second cylindrical lens 1508C has a second axis. The first axis of the first cylindrical lens 1508B is disposed at an angle of approximately 45 degrees relative to the second axis of the second cylindrical lens 1508C. In addition, in an exemplary embodiment, the first plane of the spherical lens 1508A is disposed closer to the camera 1502 than the second plane of the first cylindrical lens 1508B and the third plane of the second cylindrical lens 1508C.

Referring again to the illustrative embodiment of FIG. 16, it can be seen that the fluid control system 1506 comprises a pump 1512 and a plurality of fluid distribution lines 1514A, 1514B, 1514C. Each of the plurality of fluid distribution lines 1514A, 1514B, 1514C fluidly connects the pump to a respective one of the plurality of fluidic lenses 1508A, 1508B, and 1508C. The pump 1512 adjusts the refractive power of the plurality of fluidic lenses 1508A, 1508B, and 1508C by inserting an amount of fluid into, or removing an amount of fluid from, each of the respective chambers of the plurality of fluidic lenses 1508A, 1508B, and 1508C.

With reference again to FIG. 16, it can be seen that the illustrative automated camera system 1500 further includes a data processing device 1516, which may be in the form of a personal computing device or personal computer. The data processing device 1516 (i.e., computer) of the automated camera system 1500 may comprise a microprocessor for processing data, memory (e.g., random access memory or RAM) for storing data during the processing thereof, and data storage device(s), such as one or more hard drives, compact disk drives, floppy disk drives, flash drives, or any combination thereof. At least one visual display device (i.e., monitor or display) may be operatively coupled to the data processing device 1516 (i.e., computer). Also, a plurality of user data input devices, such as a keyboard and a mouse, may be operatively coupled to the data processing device 1516 (i.e., computer) so that a user is able to enter data into the data processing device 1516.

As shown in FIG. 16, the data processing device 1516 (i.e., computer) is operatively connected to the pump 1512 of the fluid control system 1506 by, for example, a wired connection or a wireless connection. Also, the data processing device 1516 (i.e., computer) is operatively connected to the Shack-Hartmann sensor assembly 1510 by a wired connection or a wireless connection. The data processing device (i.e., computer) is specifically programmed to control the operation of the pump 1512 of the fluid control system 1506 based upon one or more output signals from the Shack-Hartmann sensor assembly 1510. Also, as shown in FIG. 16, the data processing device 1516 (i.e., computer) is operatively coupled to the camera 1502 by, for example, a wired connection or a wireless connection. When the Shack-Hartmann sensor assembly 1510 indicates to the data processing device 1516 (i.e., computer) that the object 1504 is in focus for the camera 1502, the data processing device 1516 is specially programmed to emit one or more initiation signals to the camera 1502 instructing the camera to capture the image of the object 1504. That is, the data processing device 1516 initiates a recording by the camera 1502 (e.g., a single photograph or a movie/video) or initiates an action, such as surveillance of an area with in-focus photos (i.e., if the camera 1502 is in the form of a video surveillance camera). As also shown in FIG. 16, an on-off switch 1526 may be provided to activate or deactivate the functionality of the automated camera system 1500 described herein. That is, when the on-off switch 1526 is in the "on" position, the data processing device 1516 automatically controls the operation of the camera 1502 by means of the one or more initiation signals that automatically initiate the capturing of the image (i.e., the automatic mode). Conversely, when the on-off switch 1526 is in the "off" position, the camera 1502 is in the non-automatic mode, whereby the operation of the camera 1502 is manually controlled by a user thereof (e.g., the user is required to manually focus the camera 1502 in the non-automatic mode).

In FIG. 16, it can be seen that the Shack-Hartmann sensor assembly 1510 comprises a charge-coupled device (CCD) array 1518 and a lenslet array 1520. The charge-coupled device (CCD) array 1518 of the Shack-Hartmann sensor assembly 1510 is operatively connected to the data processing device 1516 (i.e., computer) by, for example, a wired connection or a wireless connection. Also, as shown in FIG. 16, the automated camera system 1500 further includes a dichroic mirror 1522 disposed in front of the plurality of fluidic lenses 1508A, 1508B, and 1508C. The dichroic mirror 1522 is located between the plurality of fluidic lenses 1508A, 1508B, and 1508C and the lenslet array 1520 of Shack-Hartmann sensor assembly 1510 in the path of the light. The dichroic mirror 1522 allows the light rays 1532 from the external light source outside the automated camera system 1500 to pass therethrough (as indicated by arrow 1532 in FIG. 16). The external light source could be sunlight, an artificial flash light, or an external source that generates an infrared light. The external light source illuminates the object 1504 that is being photographed or recorded by the camera 1502. The automated camera system 1500 additionally includes a first diffractive lens 1524 or a holographic optical element (HOE) disposed between the dichroic mirror 1522 and the lenslet array 1520 in the path of the light. A holographic optical element (HOE) is essentially a diffractic element, but it is made with the technique of a hologram, which results in a very thin diffractive film. A holographic optical element (HOE) is easily reproducible and inexpensive to fabricate. The first diffractive lens 1524 or holographic optical element (HOE) directs the portion 1538 of the light that is reflected from the dichroic mirror 1522 to a single focal point 1540. After passing through the single focal point 1540, the reflected light passes through a second diffractive lens 1528 before entering the lenslet array 1520 of the Shack-Hartmann sensor assembly 1510. The first and second diffractive lens 1524, 1528 are required in the automated camera system 1500 in order to maintain the fidelity of the reflected light 1538. In order to avoid obscuring the image being captured by the camera 1502, the Shack-Hartmann sensor assembly 1510 must be located outside of the direct focal line of the camera 1502.

Now, with reference again to FIG. 16, the functionality of the automated camera system 1500 of FIG. 16 will be described. Initially, as explained above, the light rays 1532 from the external light source pass through dichroic mirror 1522 and the plurality of fluidic lenses 1508A, 1508B, and 1508C, and then, are reflected back from the camera 1502 (i.e., reflected light 1534 in FIG. 16). As shown in FIG. 16, the light waves or rays 1534 that are reflected back from the camera 1502 initially pass through the plurality of fluidic lenses 1508A, 1508B, and 1508C. In particular, the light waves pass through the spherical fluidic lens 1508A first, then followed by the first cylindrical fluidic lens 1508B, and finally the second cylindrical fluidic lens 1508C. After passing through the plurality of fluidic lenses 1508A, 1508B, and 1508C, a first portion 1536 of the reflected light 1534 passes back through the dichroic mirror 1522 to the outside, while a second portion 1538 of the reflected light 1534 is reflected by the dichroic mirror 1522 through the first diffractive lens 1524. As explained above, the first diffractive lens 1524 directs the second portion 1538 of the light that is reflected from the dichroic mirror 1522 to a single focal point 1540. After passing through the single focal point 1540, the reflected light 1538 passes through a second diffractive lens 1528 before entering the lenslet array 1520 of the Shack-Hartmann sensor assembly 1510. After the light waves are transmitted to the lenslet array 1520 of the Shack-Hartmann sensor assembly 1510, a light spotfield is created on the charge-coupled device (CCD) array or CCD camera 1518 of the Shack-Hartmann sensor assembly 1510 so that the intensity and location of each light spot in the spotfield may be determined. When light spots in the spotfield are crisp and clear in the Shack-Hartmann sensor assembly 1510, they are in focus. Conversely, when light spots in the spotfield are fuzzy in the Shack-Hartmann sensor assembly 1510, they are not in focus. When all of the light spots in the spotfield are in focus, the subject of the photography (i.e., object 1504) is in focus for the camera 1502. Upon determining the intensity and location information from the spotfield, the Shack-Hartmann sensor assembly 1510, by means of the data processing device 1516, controls the refractive power of the lenses 1508A, 1508B, and 1508C through the computerized fluid pump 1512 connected to the fluidic lenses 1508A, 1508B, and 1508C. When the Shack-Hartmann sensor assembly 1510 indicates that the object 1504 of view (a landscape, person, etc.) is in focus for the camera 1502, the data processing device 1516 is specially programmed to emit one or more initiation signals to the camera 1502 so as to initiate the recording of a photo or video, with a flash or without a flash light using infra-red light.

Figures 17, 18:
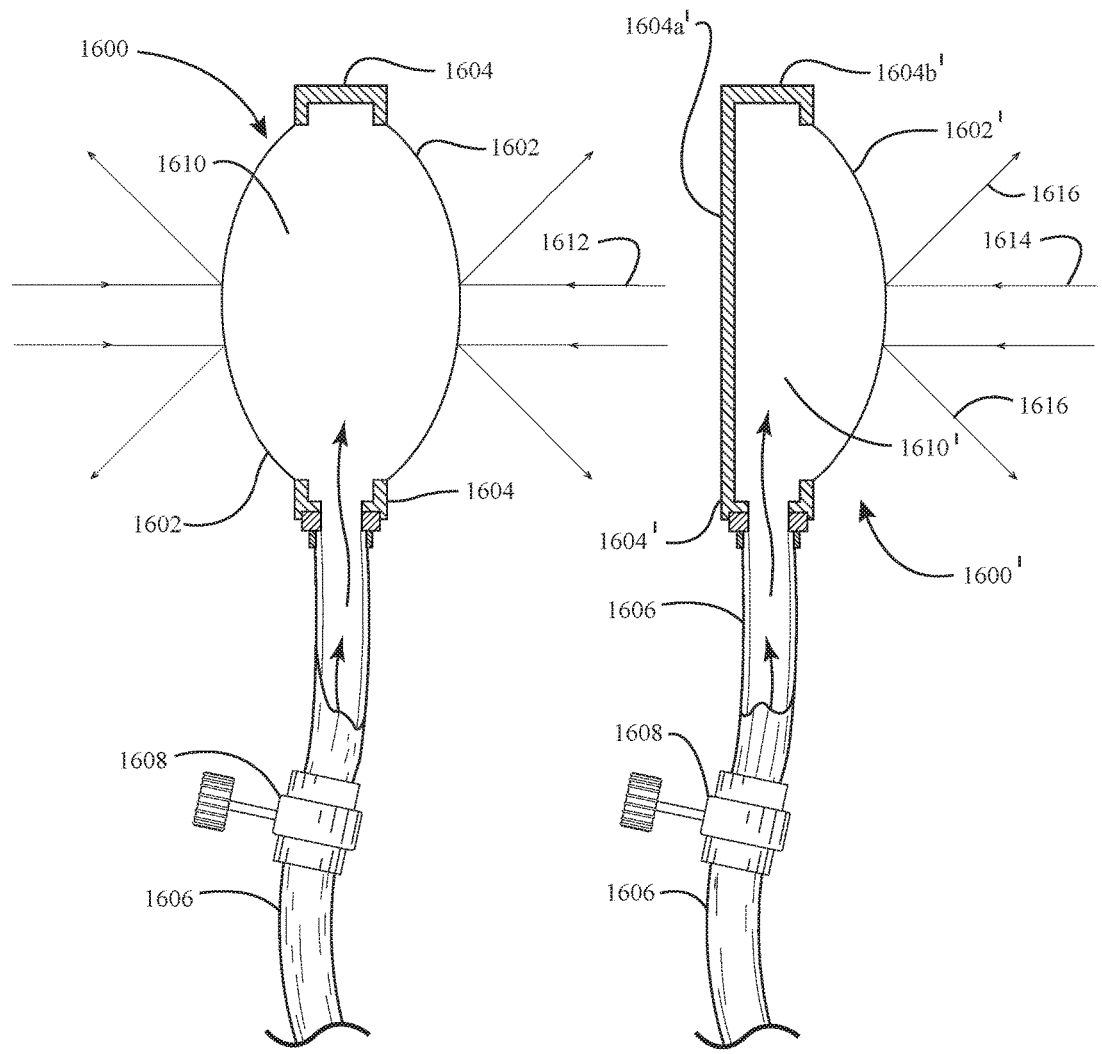
FIG. 17 is a side sectional view of a biconvex, flexible fluidic mirror, according to an embodiment of the invention.
FIG. 18 is a side sectional view of a convex, flexible fluidic mirror, according to another embodiment of the invention, wherein the section is generally cut along the cutting-plane line A-A in FIG. 19.
Figure 19:
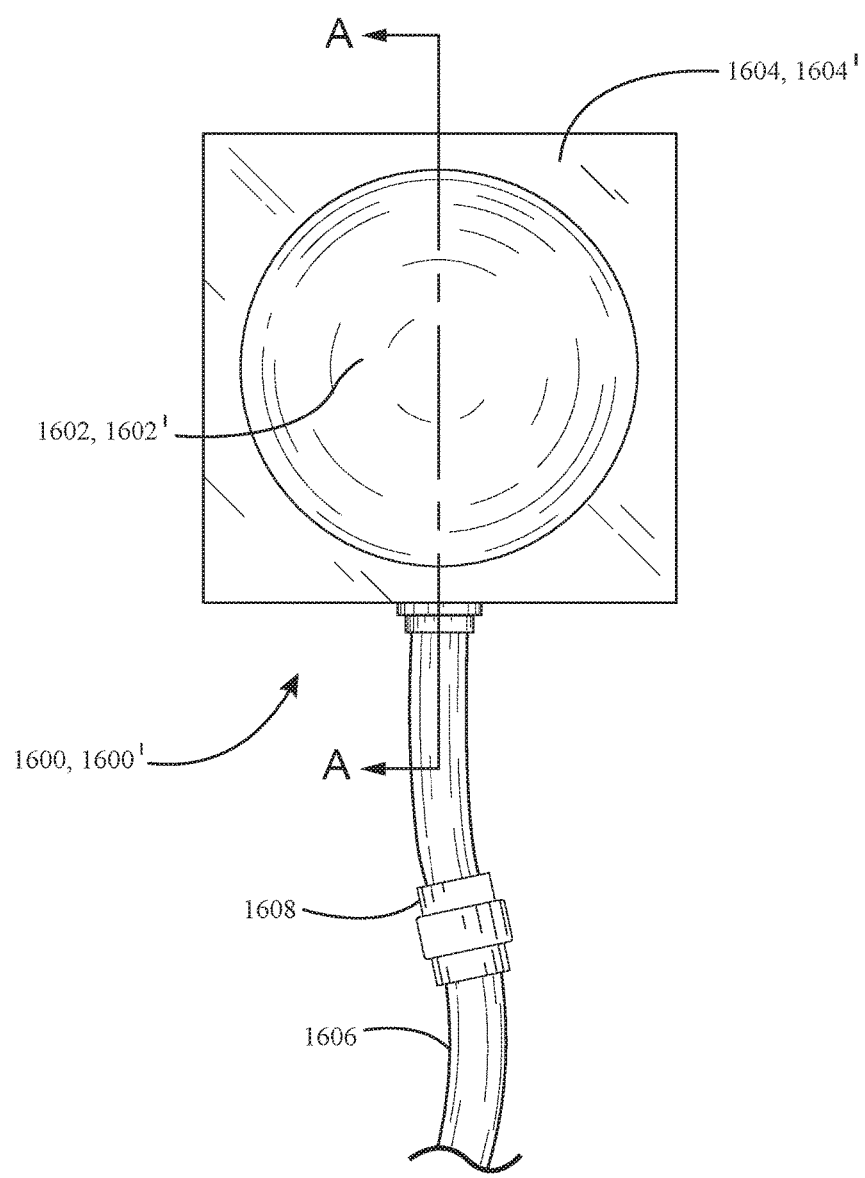
FIG. 19 is a front/top view of the convex, flexible fluidic mirrors of FIGS. 17 and 18.

FIGS. 17-28 illustrate additional embodiments of the present invention. In accordance with a first set of illustrative embodiments, a flexible fluidic mirror will be described with reference to FIGS. 17-24. The flexible fluidic mirror generally comprises a flexible membrane defining a fluid chamber, and an outer housing supporting the flexible fluid membrane. The surface of the flexible membrane of the fluidic mirror may be coated with nanoparticles that reflect light back so as to create the necessary mirror effect. The flexible membrane of the fluidic mirror may be disposed in either a convex orientation or in a concave orientation depending on whether fluid is being injected into, or withdrawn from the fluid chamber or cavity. As shown in FIG. 17, the biconvex, flexible fluidic mirror 1600 comprises a flexible membrane 1602 that is convex on both sides of the mirror. The flexible membrane 1602 is supported in an outer housing 1604, and the flexible membrane 1602 and the outer housing 1604 defines an internal fluid chamber 1610 for receiving a fluid therein. A fluid pipe or tube 1606 is fluidly coupled to the fluid chamber 1610 of the fluidic mirror 1600 so that the fluid may be injected into, or withdrawn from the fluid chamber 1610 by means of a fluid pump (e.g., the fluid pump 1512 depicted in FIG. 16 may be fluidly connected to the fluid pipe 1606). Also, referring again to FIG. 17, it can be seen that the fluid pipe or tube 1606 comprises a valve 1608 disposed therein to selectively regulate the fluid flow through the fluid pipe 1606 (i.e., turn the fluid flow on or off). In FIG. 17, it can be seen that light rays 1612 are shown striking the front surface of the mirror 1600, and reflecting off the front surface of the mirror 1600. A front view (top view) of the fluidic mirror of FIG. 17 is shown in FIG. 19. As shown in FIG. 19, the outer housing 1604 of the mirror 1600 forms a circular restriction that houses the flexible membrane 1602 therein.

The flexible fluidic mirror 1600' depicted in FIG. 18 is similar to that shown in FIG. 17, except that the flexible membrane 1602' has only a single convex front portion, rather than the biconvex configuration of FIG. 17. As shown in FIG. 18, the outer housing 1604' of the mirror 1600' has a solid, rigid back portion 1604a' that does not deform as a result of fluid pressure exerted thereon. Also, similar to the embodiment of FIG. 17, the outer housing 1604' additionally comprises a solid, rigid peripheral side housing 1604b'. In FIG. 18, it can be seen that, when the incoming light beam 1614 strikes the convex mirror 1600', the light is reflected by the front surface of the mirror 1600' (as indicated by reflected light beams 1616). One or more of the reflected light beams 1616 may be transmitted via a dichroic mirror (e.g., the dichroic mirror 1522 in FIG. 16) to a diffractive lens or a holographic element (e.g., the diffractive lens 1524, 1528 in FIG. 16) to a Shack-Hartmann system (e.g., the Shack-Hartmann assembly 1510 in FIG. 16) to increase or decrease the amount of the fluid in the mirror cavity 1610' by a processing device (e.g., a computer or computing device with a microprocessor, such as the data processing device 1516 in FIG. 16) until the beam is in focus.

Figure 20:
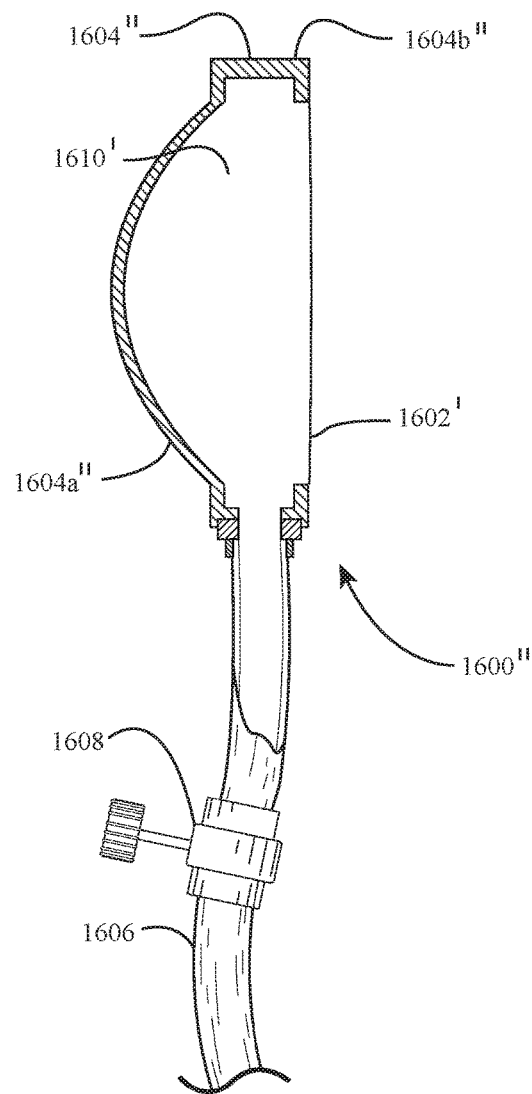
FIG. 20 is a side sectional view of a flexible concave fluidic mirror, according to yet another embodiment of the invention, wherein the flexible membrane of the mirror is in its relaxed state.
Figure 21:
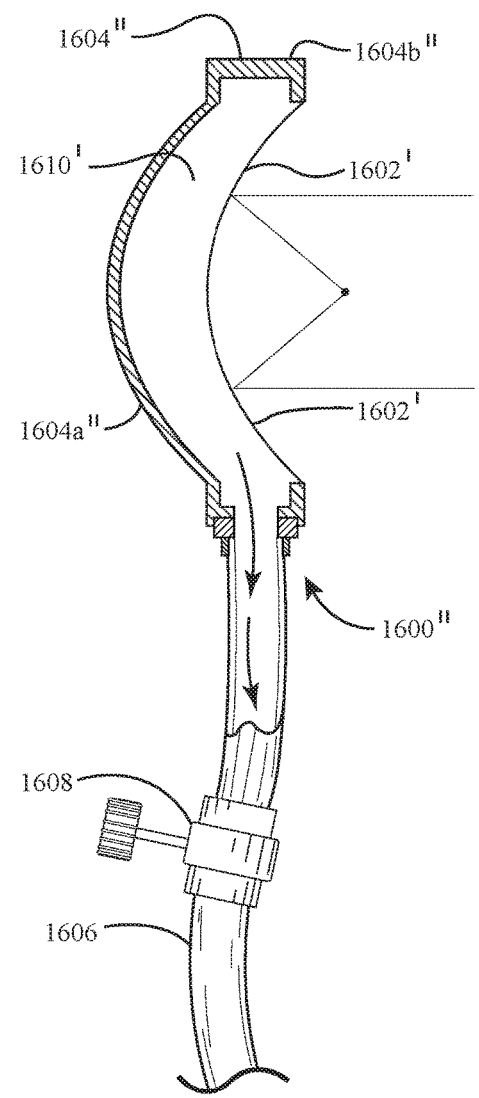
FIG. 21 is another side sectional view of the flexible concave fluidic mirror of FIG. 20, wherein the flexible membrane of the mirror is in its deformed state, and wherein the section is generally cut along the cutting-plane line B-B in FIG. 22.
Figure 22:
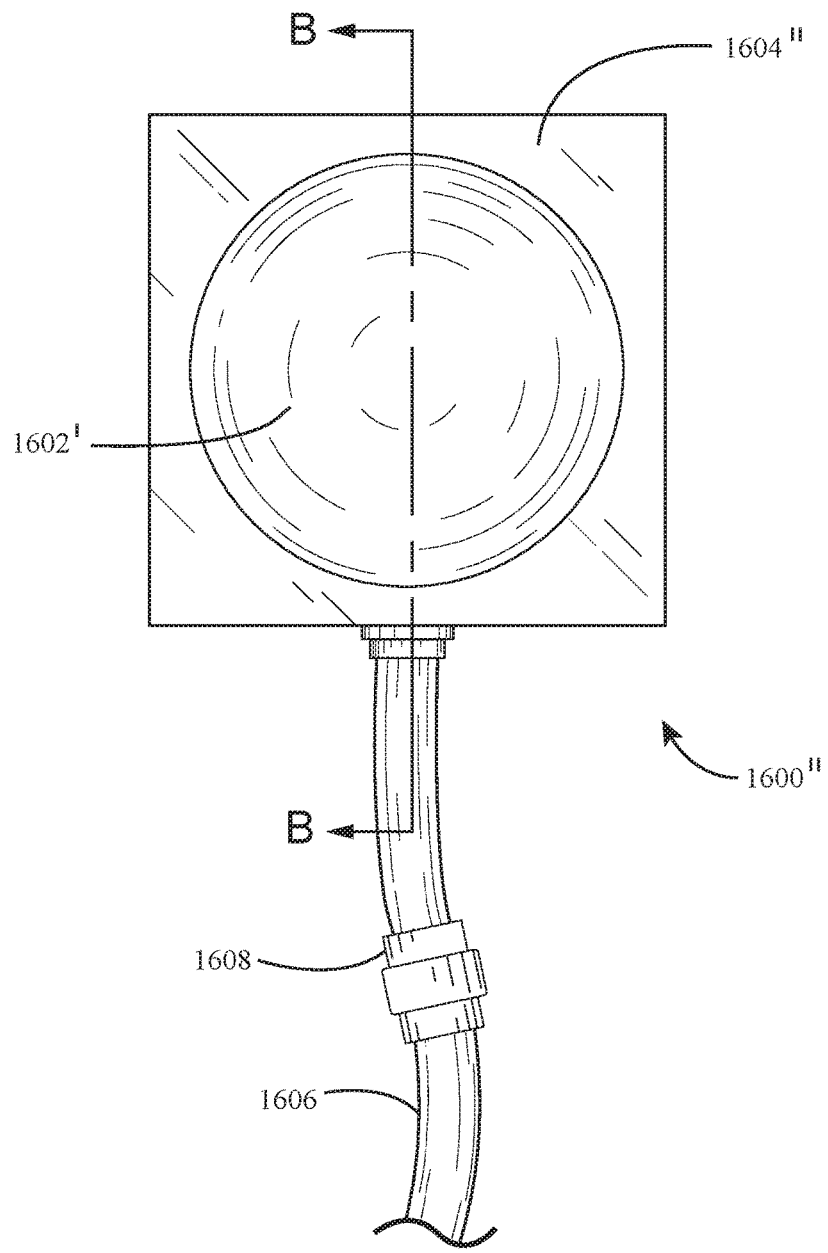
FIG. 22 is a front/top view of the flexible concave fluidic mirrors of FIGS. 20 and 21.

The circular flexible fluidic mirror 1600" depicted in FIGS. 20-22 is similar to that described above with regard to FIGS. 17 and 18, except that the flexible membrane 1602' is configured to be deformed into a concave configuration, rather than the convex configurations of FIGS. 17 and 18. As shown in the side sectional views of FIGS. 20 and 21, the outer housing 1604" of the mirror 1600" has a solid or semi-solid back portion 1604*a*" and a solid, rigid peripheral side housing 1604*b*". In FIG. 20, the flexible membrane 1602' is shown in its relaxed state, and fluid is neither flowing out of, nor into the fluid chamber 1610' of the mirror 1600". Although, in FIG. 21, fluid is depicted flowing out of the fluid chamber 1610' of the mirror 1600" through the fluid pipe 1606 in order to create the concave configuration of the mirror 1600". As shown in FIGS. 21 and 22, the solid or semi-solid back portion 1604*a*" of the mirror outer housing 1604" may be convexly-shaped in order to accommodate the concave deformation of the front flexible membrane 1602'. A front view (top view) of the fluidic mirror of FIGS. 20 and 21 is shown in FIG. 22. As shown in FIG. 22, the outer housing 1604" of the mirror 1600" forms a circular restriction that houses the flexible membrane 1602' therein.

A flexible parabolic or elliptical mirror 1600''' is depicted in FIGS. 23 and 24. As shown in the sectional side view of FIG. 24, the flexible fluidic mirror 1600''' comprises a flexible membrane 1602" that has a concave configuration (i.e., similar to the circular mirror 1600" described above with respect to FIG. 21). Also, similar to the mirrors 1600, 1600', 1600" described above, the flexible membrane 1602" is supported in an outer housing 1604''', and the flexible membrane 1602" defines an internal fluid chamber 1610" for receiving a fluid therein. Like the mirror 1600" of FIGS. 20-22, the outer housing 1604''' of the mirror 1600''' comprises a convexly-shaped solid, rigid back portion 1604*a*' and a solid, rigid peripheral side housing 1604*b*'''. In FIG. 24, fluid is depicted flowing out of the mirror 1600' through the fluid pipe 1606, which is fluidly coupled to the flexible membrane 1602", in order to create the concave/convex configuration of the mirror 1600'. Fluid may be injected into, or withdrawn from the fluid chamber 1610" of the mirror flexible membrane 1602" via the fluid pipe 1606, which is fluidly coupled to a fluid pump system (e.g., the fluid pump 1512 depicted in FIG. 16 may be fluidly connected to the fluid pipe 1606). A front view (top view) of the fluidic mirror of FIG. 24 is shown in FIG. 23. As shown in FIG. 23, the outer housing 1604''' of the mirror 1600''' forms an elliptical or oval-shaped restriction that houses the flexible membrane 1602" therein.

The surfaces of the flexible membranes 1602, 1602', 1602" of the illustrative mirrors 1600, 1600', 1600", 1600''' described above may be sprayed or coated with reflective nanoparticles that are capable of reflecting back the incoming light, such as nanoparticles of silver, iron, aluminum, zinc, gold, or another suitable metallic substance. Also, the surfaces of the flexible membranes 1602, 1602', 1602" may be sprayed, coated, or covered with a synthetic flexible reflective film to reflect the incoming light.

In one or more embodiments, the reflective coating or film disposed on the flexible membrane 1602, 1602', 1602" of the illustrative mirrors 1600, 1600', 1600", 1600''' may comprise reflective nanoparticles painted on the flexible membrane or sprayed on the flexible membrane after a polymerizable substance is cured and a desired concave or convex shape of the flexible fluidic mirror is achieved (as will be described hereinafter).

The illustrative embodiments of FIGS. 17-22 depict the manner in which a fluidic pump system may be used to modify the configurations of the flexible membranes 1602, 1602' of the circular mirrors 1600, 1600', 1600" so as to form a variety of different convex and concave configurations. The illustrative embodiment of FIGS. 23 and 24 depicts the manner in which a fluidic pump system also may be used to modify the configuration of the flexible membrane 1602" of an elliptical or parabolic mirror 1600'.

In the embodiments of FIGS. 17-24, the mirror aspect of the lens is generally limited to the front surface of the flexible membranes 1602, 1602', 1602". As such, the transparency of the back surface of the flexible membranes 1602, 1602', 1602" is generally unimportant. However, the size of the fluid chambers 1610, 1610', 1610" of the mirror flexible membranes 1602, 1602', 1602" affects the ability to move the membranes 1602, 1602', 1602" from a high convexity to a high concavity position.

In one or more embodiments, the fluid disposed in the chambers 1610, 1610', 1610" of the flexible membranes 1602, 1602', 1602" of the fluidic mirrors 1600, 1600', 1600", 1600' is in the form of a polymerizable substance so that the substance is capable of being cured after the fluidic mirrors 1600, 1600', 1600", 1600' are formed into a desired concave or convex shape. That is, after a desired deformation of the surface of the flexible membrane 1602, 1602', 1602" by means of fluid insertion or withdrawal, the polymerizable substance in the fluid cavity 1610, 1610', 1610" may be hardened or cured so that a desired mirror shape is created. In one embodiment, the polymerizable substance (e.g., a silicone oil) disposed in the chamber of the flexible fluidic mirror may be cured by the application of at least one of: (i) ultraviolet radiation, and (ii) microwaves. In another embodiment, the polymerizable substance disposed in the chamber 1610, 1610', 1610" of the fluidic mirror 1600, 1600', 1600", 1600' may comprise an initial liquid polymer and a chemical crosslinker initiator. In this embodiment, the fluidic mirror 1600, 1600', 1600", 1600''' is fixed into the desired concave or convex shape by mixing the initial liquid polymer with the chemical crosslinker initiator so as to solidify the flexible membrane 1602, 1602', 1602" and achieve the desired curvature (i.e., to harden and fix the desired curvature).

In contrast to the fluidic mirror 1600, 1600', 1600", 1600''' described above, the hybrid flexible fluidic lens that will be described hereinafter requires the fluid in the fluidic chamber of the lens to remain a liquid so that the hybrid flexible fluidic lens remains adjustable using the two different options of either fluidic adjustment or adjustment by an electromagnetic actuator. Also, as will be described hereinafter, both the front and back surfaces of the hybrid flexible fluidic lens are clear or transparent in order to allow light to pass therethrough.

In accordance with a second set of illustrative embodiments, a hybrid system that utilizes both a fluidic pump and an electrically induced magnet will be described with reference to FIGS. 25-28. A hybrid, flexible concave/convex mirror or lens is depicted in the embodiments of FIGS. 25-28. In general, in these illustrative embodiments, the control of the membrane deflection of the flexible concave/convex mirror or lens is capable of being done by two mechanisms. First of all, injection or withdrawal of the fluid from the fluid chamber of the mirror or lens is done using an electric fluid pump that is fluidly coupled to the fluid chamber of the mirror or lens via a fluid pipe or tube (e.g., the fluid pump 1512 depicted in FIG. 16 may be fluidly connected to the fluid pipe of the mirror or lens). The injection of fluid into the chamber creates a membrane with a convex surface, while the withdrawal of fluid from the chamber creates a membrane with a concave surface. Secondly, the front portion of the flexible membrane also may be under the control of a magnetic plate and actuator. Both the fluid-based and magnetic mechanisms are used by activating a sensor and a processor to achieve the desired dioptic power. The magnetic plate is capable of making the front surface of the mirror or lens membrane convex, but it is not capable of making it concave. As such, the fluidic pump system is needed to withdraw the fluid from the lens or mirror to create a concave surface. As will be described in more detail hereinafter, the motion of the frontal magnetic plate is controlled by the magnetic force generated by the electromagnetic located on the back surface of the flexible membrane or outer housing.

Advantageously, the magnetic system of the hybrid lens or mirror enables a fast refinement or adjustment of the mirror or lens. During this quick adjustment of the mirror or lens, the convexity of the flexible mirror or lens is controlled by a magnetic field generated by the magnetic system, while the valve member of the fluidic outflow tube is closed so as to prevent fluid flow through the tube. Then, an electric potential is applied to the solid plate behind the mirror or lens. By electrically increasing the magnetic field, the thin ferromagnetic plate attached on the front surface of the membrane moves backward, thus increasing the pressure in the fluidic lens. This magnetic force increases the pressure inside the mirror lens, which in turn, pushes the flexible membrane at the center of the mirror or lens forward so as to create a more convex central portion of the mirror or lens. By decreasing the magnetic field, the frontal thin magnetic plate is released, which in turn, reduces the fluidic pressure or force in the mirror or lens, and the flexible membrane of the mirror or lens retreats backwards, thereby decreasing the convexity of the flexible membrane (see e.g., FIG. 26).

Now, turning to FIGS. 25-28, the illustrative embodiments of the hybrid mirror (or lens if the membrane is not provided with a reflective coating) will be described. Initially, as shown in the side sectional view of FIG. 26, the hybrid mirror 1700 comprises a flexible membrane 1702 that is convex on the front side of the mirror. The flexible membrane 1702 of the hybrid mirror 1700 is supported in an outer housing 1704, and the flexible membrane 1702 and outer housing 1704 defines an internal fluid chamber 1710 for receiving a fluid therein. As shown in FIG. 26, the back side of the hybrid mirror 1700 may comprise a solid or semi-solid transparent back portion 1716 (e.g., a transparent pane of glass) that does not deform as a result of fluid pressure exerted thereon. A fluid pipe or tube 1706 is fluidly coupled to the fluid chamber 1710 of the fluidic mirror 1700 so that the fluid may be injected into, or withdrawn from the fluid chamber 1710 by means of a fluid pump (e.g., the fluid pump 1512 depicted in FIG. 16 may be fluidly connected to the fluid pipe 1706). Also, referring again to FIG. 26, it can be seen that the fluid pipe or tube 1706 comprises a valve 1708 disposed therein to selectively regulate the fluid flow through the fluid pipe 1706 (i.e., turn the fluid flow on or off). In addition, as illustrated in FIG. 26, a ferromagnetic annular plate 1712 is provided on the front surface of the flexible membrane 1702 for altering the shape of the front portion of the flexible membrane 1702 (i.e., by making the front portion of the flexible membrane 1702 more or less convex in shape). An electromagnetic annular plate 1714 is provided on the back panel 1716 of the hybrid mirror 1700 that selectively attracts or repels the ferromagnetic annular plate 1712 on the front surface of the flexible membrane 1702 to make the flexible membrane 1702 more convex or less convex. The magnetic force (as diagrammatically represented by the magnetic flux lines 1718 in FIG. 26) exerted by the electromagnetic back plate 1714 on the ferromagnetic front plate 1712 is selectively controlled by regulating the electrical current flow to the electromagnetic annular plate 1714. In the embodiment of FIG. 26, the fluid valve 1708 is shown in its closed position so that fine adjustments may be made to the convexity of the flexible membrane 1702 by the magnetic system 1712, 1714.

As shown in FIG. 25, the outer housing 1704 of the hybrid mirror 1700 forms a circular restriction that houses the flexible membrane 1702 therein. Also, referring to FIG. 25, it can be seen that the ferromagnetic annular plate or ring 1712 is attached to the front surface of the flexible membrane 1702 to regulate the convexity of the flexible membrane 1702. In one embodiment of FIGS. 25 and 26, the front surface of the flexible membrane 1702 is provided with a reflective surface coating so that the flexible membrane 1702 functions as a mirror. Although, in one or more alternative embodiments of FIGS. 25 and 26, the reflective surface coating may be omitted from the flexible membrane 1702, and the flexible membrane 1702 may be transparent instead so that the flexible membrane 1702 functions as a lens. When the flexible membrane 1702 functions as a lens, the transparent back portion 1716 of the housing 1704 allows light rays to pass through the back wall of the housing 1704.

Figure 28:
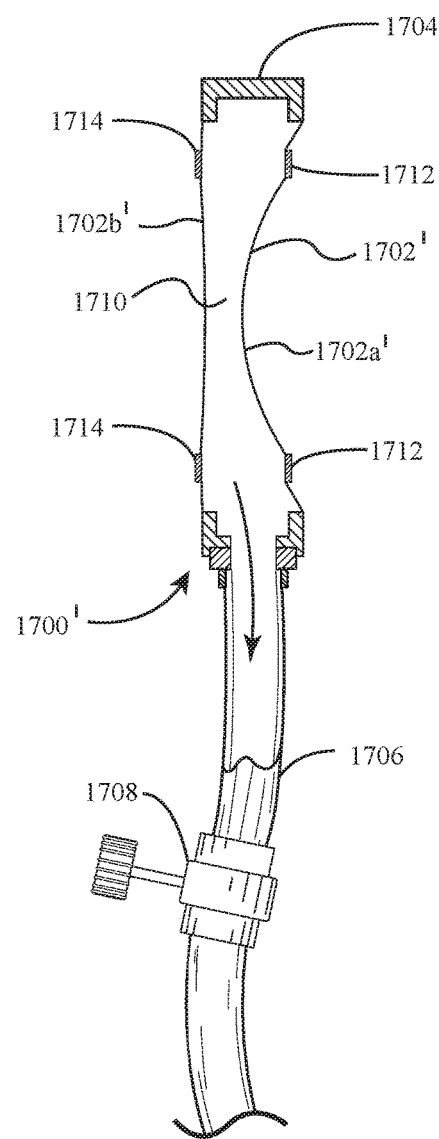
FIG. 28 is a side sectional view of another hybrid flexible fluidic mirror, according to yet another embodiment of the invention.

The circular hybrid mirror 1700' depicted in FIG. 28 is similar to that described above with regard to FIGS. 25 and 26, except that the flexible membrane 1702' has a concave front portion 1702a', rather than the convex configuration of FIGS. 25 and 26. Also, unlike the hybrid mirror 1700 of FIGS. 25 and 26, the hybrid mirror 1700' of FIG. 28 is additionally provided with a flexible rear membrane portion 1702b'. Similar to the hybrid mirror 1700 of FIGS. 25 and 26, the hybrid mirror 1700' comprises a magnetic adjustment system with a ferromagnetic annular plate or ring 1712 attached to the front surface of the front flexible membrane 1702a' and an electromagnetic annular plate 1714 attached to the back surface of the flexible rear membrane portion 1702b'. In FIG. 28, fluid is depicted flowing out of the fluid chamber 1710 of the mirror 1700' through the fluid pipe 1706 in order to create the concave configuration of the mirror 1700'.

Figure 27:
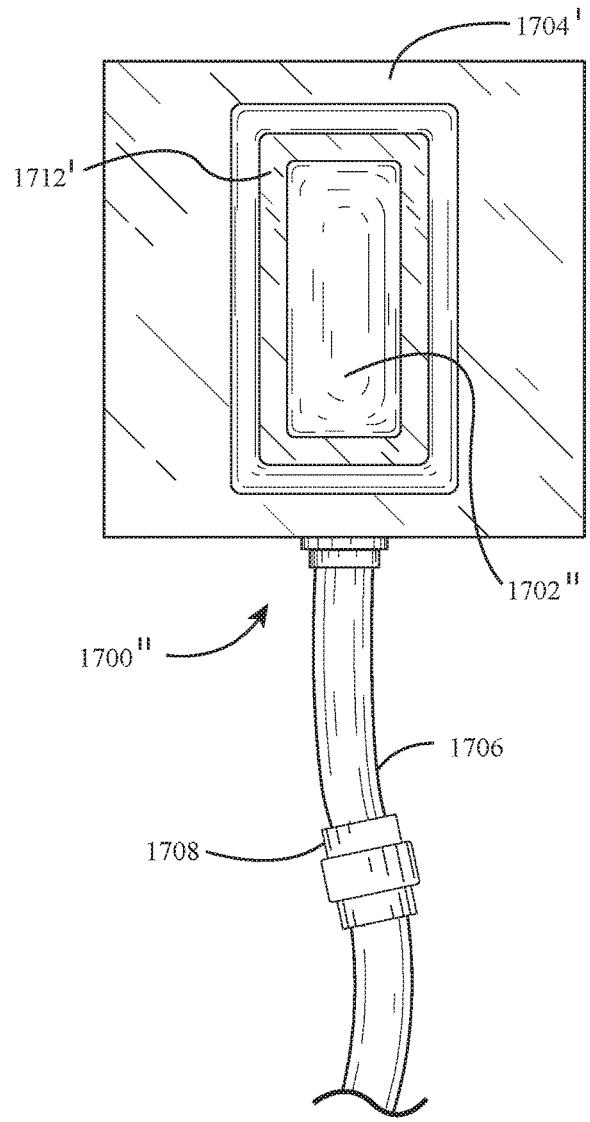
FIG. 27 is a front/top view of another hybrid flexible fluidic mirror, according to still another embodiment of the invention.

A front view (top view) of an alternative hybrid parabolic or elliptical mirror 1700" is depicted in FIG. 27. As shown in FIG. 27, the hybrid parabolic or elliptical mirror 1700" comprises an outer housing 1704' that forms a rectangular restriction that houses the flexible membrane 1702" therein. In addition, as depicted in FIG. 27, the hybrid parabolic or elliptical mirror 1700" comprises a ferromagnetic rectangular plate 1712' attached to the front surface of the flexible membrane 1702". A corresponding electromagnetic rectangular plate is provided on the back side of the housing 1704' that selectively attracts or repels the ferromagnetic rectangular plate 1712' on the front surface of the flexible membrane 1702" to make the flexible membrane 1702" more convex or less convex.

In one or more embodiments, if the flexible membrane is made flexible and transparent and the center of the back plate of the housing is also transparent (e.g., as shown in FIG. 26), the hybrid lens may also function as a refractive lens, a spherical fluidic lens, or astigmatic fluidic lens.

Alternatively, if the flexible membrane is coated with reflective nanoparticles (as described above with respect to the flexible fluidic mirror of FIGS. 17-24), the hybrid system may be used as a mirror system.

In the illustrative embodiments of FIGS. 25-28, the entire hybrid mirror or lens control system, which includes the fluidic pump (e.g., pump 1512 in FIG. 16) and the electromagnet that generates the magnetic field, is under control of a sensor (e.g., Shack-Hartmann sensor assembly 1510, as shown in FIG. 16), which is connected to the fluidic mirrors or lenses via a specially programmed computer (e.g., the data processing device 1516 depicted in FIG. 16) that focuses the images properly for the functions as described above. The operator may also manually take over the control of the lenses if used in glasses or in a camera, etc.

The hybrid system of FIGS. 25-28 combines a fluid-based mirror or lens system with an electromagnetic force-based system that compresses the membrane of the mirror or lens for making fine adjustments thereto. The fluid injection and withdrawal ability of the hybrid system enables the fluidic lenses to assume either a convex surface (i.e., to operate as a plus lens) or a concave surface (i.e., to operate as a minus lens).

In one or more embodiments, the fluidic portion of the system may provide corrections ranging from −30.00 diopters (D) to +30.00 diopters (D), or more diopters (D) power at a step of 0.1 diopters (D), while the compressive part may add further adjustability to the system by adding small step corrections of 0.001 diopters (D), all under the control of the Shack-Hartmann system (e.g., Shack-Hartmann system 1510 in FIG. 16). Thus, this system provides an extremely high resolution that conventional solid lenses cannot achieve. Presently, conventional solid lenses are capable of correcting the refractive power from −0.25 D to +0.25 D.

In one or more embodiments, the refractive power of the fluidic lenses are uniformly controlled by the Shack-Hartmann sensor as a result of the fluidic pump injecting or withdrawing the fluid from the lens chambers via a processor (i.e., a computing device with a microprocessor).

In one or more other embodiments, the control of the refractive power of the lenses is performed with a hybrid lens system and a Shack-Hartmann sensor by: (a) injecting or withdrawing of fluid in some lenses, and (b) in the remaining lenses of the system, using a compressive ring-shaped magnetic plate 1712 (e.g., see FIG. 25) or rectangular frame shaped magnetic plate 1712' (e.g., see FIG. 27) located on the front (or alternatively on the back surface) of the fluidic lens. The compressive ring-shaped magnetic plate 1712 or the rectangular frame shaped magnetic plate 1712' may be moved forward or backward by an electromagnet located in the frame or the fluidic lens, like a solenoid. When the magnet is activated, it attracts the magnetic ring 1712 or the rectangular plate 1712', thereby compressing the internal lens fluid without causing the internal lens fluid to escape. The compression of the internal lens fluid forces the center of the lens membrane forward, thus making the curvature of the lens surface more or less convex, depending on the amount of force generated by the electromagnet. This force produces either a more convex spherical surface if the plate is ring-shaped or a more cylindrical lens if the restrictive plate is rectangular shaped.

In another embodiment, two (2) cylindrical lenses positioned forty-five (45) degrees from each other are activated with an electromagnetic force to compensate for astigmatic correction, while the spherical lens remains as a non-hybrid fluidic lens. The magnetically controlled cylindrical lenses, which perform correct cylindrical correction, together with the non-hybrid fluid spherical lens provides a complete hybrid combination lenses system and has the ability to provide collectively a refractive power of plus cylinder of 0.1−+10 D and a spherical correction of −30 D to +25 D or more diopters at any axis controlled by the Shack-Hartmann sensor through a processor (i.e., a computing device with a microprocessor).

This hybrid combination system, controlled by a sensor such as a Shack-Hartmann sensor, provides an automated camera which maintains the object in the focal plane at all times, regardless of the status of the object (i.e., whether it is still or in motion).

Other applications of the hybrid system may be used in a digital automatic recording camera, an endoscope, a surveillance camera, a motion picture camera, a military or a sport rifle, a remote controlled robotic system, an operating microscope, a perimetry unit used for evaluation of the visual field, a laboratory microscope, a lensometer, a system of two photon or multiphoton microscopy, confocal microscopy, optical coherence tomography (OCT), astronomical telescopes, etc. The hybrid system may also be used in other systems that are familiar in the art.

In one or more embodiments, the aforedescribed mirror (i.e., mirror 1600 or hybrid mirror 1700) may be equipped with a sensor that is capable of controlling the focal point of the fluidic mirror via a processor. The sensor may be a laser beam measuring the distance from an object to the mirror, the sensor may be a Shack-Hartmann sensor, or other means known in the art to focus and sharpen the image obtained by a telescope or focus the image on the object, such as in ophthalmic photography, or laser use in an elliptical mirror for the ophthalmology, etc.

It is readily apparent that the aforedescribed flexible fluidic mirror and hybrid system offer numerous advantages. First, the flexible fluidic mirror, which may be used as a concave mirror by adjusting the fluid amount therein, is generally easy and inexpensive to produce. In addition, the fluidic concave, elliptical, and parabolic mirrors described above are capable of being readily adjusted when needed, without requiring expensive movable parts. In particular, the refractive power of the surfaces of the inventive flexible fluidic mirrors described herein are capable of being easily adjusted so that the systems in which the fluidic mirrors are incorporated may be automated, and the images acquired by the systems may be automatically in focus when under the control of a sensor. Advantageously, the aforedescribed flexible fluidic mirrors may be easily produced for a wide variety of different applications, such as automobile industry side mirrors and telescope mirrors. Because these mirrors are easily adjustable, they are capable of being used to track a fast moving object. These mirrors also may be used for still photography, and for video applications. As described above, because the concave fluidic mirrors may also be elliptical or parabolic (e.g., see FIG. 23), they also may be effectively used in wide angle photography, optical coherence tomography (OCT), angiography, etc. Also, the aforedescribed flexible fluidic mirrors may be utilized in ophthalmology for visualization, photography or laser treatment of retina, lens, or cornea lesions located on a surface area, etc. The flexible fluidic mirrors are also useful in remote laser systems, such as the remote laser-imaging systems described in U.S. Pat. Nos. 8,452,372, 8,903,468 and 9,037, 217, the disclosures of each of which are incorporated by reference herein in their entireties. For example, the solid, non-flexible elliptical mirror 220 in the wide angle camera of the remote laser-imaging systems described in U.S. Pat.

Nos. 8,452,372, 8,903,468 and 9,037,217, may be replaced with the flexible fluidic mirror described herein.

In addition, the fluidic mirrors 1600, 1700 described herein may be used in other applications requiring concave surfaces in ophthalmology that conventionally employ fixed surfaces, such as in corneal topography equipment used for external imaging, or for three dimensional (3D) eye imaging devices that use rotating cameras. The mirrors in this type of equipment are used for doing perimetry to evaluate the visual field of a patient, or for doing electrophysiolgic evaluation of the retina (ERG) electroretinogram, or visual evoked potential (VEP) for evaluation of the function of the retina, optic nerve and the occipital brain cortex, in numerous diseases including traumatic brain injuries (TBIs), Alzheimer's disease, etc.

Any of the features or attributes of the above described embodiments and variations can be used in combination with any of the other features and attributes of the above described embodiments and variations as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A flexible fluidic mirror system, comprising:
   a flexible fluidic mirror having an outer housing and a flexible membrane supported within the outer housing, the flexible membrane at least partially defining a chamber that receives a fluid therein, a portion of the flexible membrane comprising a reflective coating of nanoparticles adhered to the flexible membrane that reflects one or more incoming light beams, and the flexible membrane of the flexible fluidic mirror being disposed within a front aperture of the outer housing, and wherein the outer housing of the flexible fluidic mirror comprises a solid, rigid rear wall that is disposed generally opposite to the flexible membrane, the solid, rigid rear wall of the outer housing of the flexible fluidic mirror having a flat peripheral portion and a convexly-shaped central portion projecting outwardly from the flat peripheral portion, the convexly-shaped central portion of the solid, rigid rear wall of the outer housing accommodating the flexible membrane being deformed into a concave shape;
   a fluid control system operatively coupled to the flexible fluidic mirror, the fluid control system configured to insert an amount of the fluid into the chamber of the flexible fluidic mirror, or remove an amount of the fluid from the chamber of the flexible fluidic mirror, in order to change the shape of the flexible fluidic mirror in accordance with the amount of fluid therein; and
   a Shack-Hartmann sensor assembly operatively coupled to the fluid control system, at least one of the one or more incoming light beams reflected by the flexible fluidic mirror being transmitted to the Shack-Hartmann sensor assembly, the Shack-Hartmann sensor assembly by means of the fluid control system automatically controlling the amount of the fluid in the chamber of the flexible fluidic mirror, thereby automatically changing the shape of the flexible fluidic mirror based upon the at least one of the one or more incoming light beams that is transmitted to the Shack-Hartmann sensor assembly, and the Shack-Hartmann sensor assembly further controlling the focal point of the flexible fluidic mirror by means of a data processing device operatively coupled to the fluid control system.

2. The flexible fluidic mirror system of claim 1, wherein the flexible membrane of the flexible fluidic mirror comprises a front surface that is generally circular, rectangular, or elliptical in shape, and wherein the front aperture of the outer housing of the flexible fluidic mirror is circular, rectangular, or elliptical in shape so as to form the generally circular, rectangular, or elliptical shape of the flexible membrane front surface.

3. The flexible fluidic mirror system of claim 1, wherein the fluid control system comprises a pump and one or more fluid distribution lines, at least one of the one or more fluid distribution lines fluidly coupling the pump to the flexible fluidic mirror so that the pump is capable of adjusting concavity and/or convexity of the flexible fluidic mirror.

4. The flexible fluidic mirror system of claim 1, wherein the fluid disposed in the chamber of the flexible fluidic mirror is in the form of a polymerizable substance that is cured after the flexible fluidic mirror is formed into a desired concave or convex shape.

5. The flexible fluidic mirror system of claim 4, wherein the polymerizable substance disposed in the chamber of the flexible fluidic mirror is cured by the application of at least one of: (i) ultraviolet radiation, and (ii) microwaves.

6. The flexible fluidic mirror system of claim 5, wherein the nanoparticles forming the reflective coating of the flexible membrane are painted on the flexible membrane or sprayed on the flexible membrane after the polymerizable substance is cured and the desired concave or convex shape of the flexible fluidic mirror is achieved.

7. The flexible fluidic mirror system of claim 4, wherein the polymerizable substance disposed in the chamber of the flexible fluidic mirror comprises a liquid polymer and a chemical crosslinker initiator, and wherein the flexible fluidic mirror is affixed into the desired concave or convex shape by mixing the liquid polymer with the chemical crosslinker initiator so as to solidify the flexible membrane and achieve the desired curvature.

8. The flexible fluidic mirror system of claim 1, further comprising a valve for regulating a flow of the fluid into, or out of, the chamber of the flexible fluidic mirror.

9. The flexible fluidic mirror system of claim 1, wherein the fluid control system comprises a single pump and one or more fluid distribution lines, a single one of the one or more fluid distribution lines fluidly coupling the single pump to the outer housing of the flexible fluidic mirror so that the single pump is capable of adjusting concavity and/or convexity of the flexible fluidic mirror, the single pump configured to both insert an amount of the fluid into the chamber of the flexible fluidic mirror, and remove an amount of the fluid from the chamber of the flexible fluidic mirror.

10. The flexible fluidic mirror system of claim 9, wherein the data processing device is operatively coupled to the single pump of the fluid control system and the Shack-Hartmann sensor assembly, and wherein the data processing device controls an operation of the single pump of the fluid control system based upon one or more output signals from the Shack-Hartmann sensor assembly.

11. The flexible fluidic mirror system of claim 1, wherein the nanoparticles forming the reflective coating of the flexible membrane are selected from the group consisting of iron nanoparticles, aluminum nanoparticles, zinc nanoparticles, and gold nanoparticles.

12. The flexible fluidic mirror system of claim 1, wherein the flexible membrane of the flexible fluidic mirror comprises a front surface with a periphery that is generally elliptical in shape, and wherein the front aperture of the outer housing of the flexible fluidic mirror is elliptical in shape so as to form the generally elliptical shape of the flexible membrane front surface.

13. A flexible fluidic mirror system, comprising:

a flexible fluidic mirror having an outer housing and a flexible membrane supported within the outer housing, the flexible membrane at least partially defining a chamber that receives a fluid therein, a portion of the flexible membrane comprising a reflective coating of nanoparticles adhered to the flexible membrane that reflects one or more incoming light beams, and the flexible membrane of the flexible fluidic mirror comprising a front membrane portion disposed within a front aperture of the outer housing and a rear membrane portion disposed within a rear aperture of the outer housing such that the flexible fluidic mirror is in the form of a biconvex fluidic mirror;

a fluid control system operatively coupled to the flexible fluidic mirror, the fluid control system configured to insert an amount of the fluid into the chamber of the flexible fluidic mirror, or remove an amount of the fluid from the chamber of the flexible fluidic mirror, in order to change the shape of the flexible fluidic mirror in accordance with the amount of fluid therein; and a Shack-Hartmann sensor assembly operatively coupled to the fluid control system, at least one of the one or more incoming light beams reflected by the flexible fluidic mirror being transmitted to the Shack-Hartmann sensor assembly, the Shack-Hartmann sensor assembly by means of the fluid control system automatically controlling the amount of the fluid in the chamber of the flexible fluidic mirror, thereby automatically changing the shape of the flexible fluidic mirror based upon the at least one of the one or more incoming light beams that is transmitted to the Shack-Hartmann sensor assembly, and the Shack-Hartmann sensor assembly further controlling the focal point of the flexible fluidic mirror by means of a data processing device operatively coupled to the fluid control system.

* * * * *